US008283135B2

(12) United States Patent
Doyle et al.

(10) Patent No.: US 8,283,135 B2
(45) Date of Patent: Oct. 9, 2012

(54) ORAL CARE COMPOSITIONS CONTAINING COMBINATIONS OF ANTI-BACTERIAL AND HOST-RESPONSE MODULATING AGENTS

(75) Inventors: Matthew Joseph Doyle, Cincinnati, OH (US); Leo Timothy Laughlin, Mason, OH (US); Todd Laurence Underiner, Cincinnati, OH (US); Begonia Y. Ho, Cincinnati, OH (US); Rowan Andrew Grayling, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 469 days.

(21) Appl. No.: 11/595,530

(22) Filed: Nov. 10, 2006

(65) Prior Publication Data

US 2007/0053849 A1    Mar. 8, 2007

Related U.S. Application Data

(63) Continuation-in-part of application No. 09/607,602, filed on Jun. 30, 2000, now abandoned.

(51) Int. Cl.
*A61K 7/16* (2006.01)
(52) U.S. Cl. ........................................................ 435/49
(58) Field of Classification Search ...................... 424/49
See application file for complete search history.

(56) References Cited

U.S. PATENT DOCUMENTS

| | | |
|---|---|---|
| 2,946,725 A | 7/1960 | Norris et al. |
| 3,864,472 A | 2/1975 | Pensak et al. |
| 4,042,679 A | 8/1977 | Gaffar |
| 4,051,234 A | 9/1977 | Gieske et al. |
| 4,080,441 A | 3/1978 | Gaffar et al. |
| 4,089,880 A | 5/1978 | Sullivan |
| 4,100,270 A | 7/1978 | Gaffar |
| 4,102,993 A | 7/1978 | Gaffar |
| 4,110,429 A | 8/1978 | Gaffar et al. |
| 4,118,472 A | 10/1978 | Gaffar |
| 4,118,473 A | 10/1978 | Gaffar et al. |
| 4,118,474 A | 10/1978 | Gaffar et al. |
| 4,118,475 A | 10/1978 | Gaffar et al. |
| 4,118,476 A | 10/1978 | Gaffar et al. |
| 4,123,512 A | 10/1978 | Gaffar |
| 4,137,303 A | 1/1979 | Gaffar et al. |
| 4,188,372 A | 2/1980 | Gaffar |
| 4,206,215 A | 6/1980 | Bailey |
| 4,224,309 A | 9/1980 | Gaffar et al. |
| 4,256,730 A | 3/1981 | Benedict |
| 4,273,759 A | 6/1981 | Gaffar |
| 4,323,551 A | 4/1982 | Parran |
| 4,325,939 A | 4/1982 | Shah |
| 4,339,430 A | 7/1982 | Gaffar |
| 4,370,314 A | 1/1983 | Gaffar |
| 4,472,373 A | 9/1984 | Ryan |
| 4,599,228 A | 7/1986 | Ladanyi |
| 4,663,154 A | 5/1987 | Ryan |
| 4,894,220 A | 1/1990 | Nabi et al. |
| 4,959,204 A | 9/1990 | Ryan |
| 4,994,262 A | 2/1991 | Charbonneau et al. |
| 5,004,597 A | 4/1991 | Majeti et al. |
| 5,015,466 A | 5/1991 | Parran, Jr. et al. |
| 5,158,763 A | 10/1992 | Gaffar |
| 5,256,396 A | 10/1993 | Piechota, Jr. |
| 5,258,173 A | 11/1993 | Waterfield |
| 5,286,479 A | 2/1994 | Garlich et al. |
| 5,292,527 A | 3/1994 | Konopa |
| 5,294,433 A | 3/1994 | Singer et al. |
| 5,356,615 A | 10/1994 | Gaffar |
| 5,364,616 A | 11/1994 | Singer et al. |
| 5,370,865 A | 12/1994 | Yamagishi et al. |
| 5,374,418 A | 12/1994 | Oshino et al. |
| 5,405,604 A | 4/1995 | Hall |
| 5,407,664 A | 4/1995 | Konopa |
| 5,431,927 A | 7/1995 | Hand et al. |
| 5,464,609 A | 11/1995 | Kelm et al. |
| 5,525,330 A | 6/1996 | Gaffar et al. |
| 5,560,906 A | 10/1996 | Scodari et al. |
| 5,578,293 A | 11/1996 | Prencipe et al. |
| 5,626,837 A | 5/1997 | Shimada et al. |
| 5,639,746 A | 6/1997 | Yelm |
| 5,646,174 A | 7/1997 | Kelm et al. |
| 5,656,591 A | 8/1997 | Tomita et al. |
| 5,672,598 A | 9/1997 | De et al. |
| 5,681,549 A | 10/1997 | McLaughlin et al. |

(Continued)

FOREIGN PATENT DOCUMENTS

| | | |
|---|---|---|
| CN | 1075868 | 9/1993 |
| CN | 1086995 | 5/1994 |
| CN | 1213534 | 4/1995 |
| CN | 1103776 | 6/1995 |
| CN | 1109742 | 10/1995 |
| EP | 0 430 474 | 6/1991 |
| GB | 2 290 233 | 12/1995 |
| JP | 04 089428 A | 3/1992 |
| JP | 06 305945 A | 11/1994 |
| JP | 11 139947 | 5/1999 |

(Continued)

OTHER PUBLICATIONS

U.S. Appl. No. 09/607,602, filed Jun. 30, 2000.
U.S. Appl. No. 11/409,850, filed Apr. 24, 2006.
U.S. Appl. No. 09/607,240, filed Jun. 30, 2000.
U.S. Appl. No. 10/454,843, filed Jun. 5, 2003.
U.S. Appl. No. 11/037,560, filed Jan. 18, 2005.

(Continued)

*Primary Examiner* — Ralph Gitomer

(57) ABSTRACT

The present invention encompasses topical oral care compositions comprising the combination of an anti-bacterial agent with an anti-inflammatory agent in an orally acceptable carrier for effective treatment and prevention of bacteria-mediated diseases and conditions in the oral cavity and for modulating host reaction to bacterial pathogens present in the oral cavity and to the toxins, endotoxins, inflammatory cytokines and mediators released by or prompted by these pathogens. The present invention also encompasses methods of use of these compositions comprising topical application to the oral cavity. The benefits of the present compositions and methods extend beyond treating and preventing oral bacterial infections in the oral cavity to promoting whole body or systemic health.

6 Claims, No Drawings

U.S. PATENT DOCUMENTS

| | | | |
|---|---|---|---|
| 5,686,063 A | | 11/1997 | McLaughlin et al. |
| 5,747,004 A | * | 5/1998 | Giani et al. .................... 424/49 |
| 5,753,217 A | | 5/1998 | Christopfel et al. |
| 5,780,046 A | | 7/1998 | Humber et al. |
| 5,785,951 A | | 7/1998 | Kelm et al. |
| 5,830,511 A | | 11/1998 | Mullerat et al. |
| 5,830,915 A | | 11/1998 | Pikul et al. |
| 5,875,798 A | | 3/1999 | Petrus |
| 5,875,799 A | | 3/1999 | Petrus |
| 5,939,052 A | | 8/1999 | White, Jr. et al. |
| 5,945,087 A | | 8/1999 | Nelson et al. |
| 5,948,390 A | | 9/1999 | Nelson et al. |
| RE36,419 E | | 11/1999 | Cavanaugh, Jr. |
| 5,980,925 A | | 11/1999 | Jampani et al. |
| 6,004,587 A | | 12/1999 | Mullerat et al. |
| 6,015,912 A | | 1/2000 | Wang et al. |
| 6,117,417 A | | 9/2000 | Wicks et al. |
| 6,190,644 B1 | | 2/2001 | McClanahan et al. |
| 6,241,974 B1 | | 6/2001 | White, Jr. et al. |
| 6,344,187 B1 | | 2/2002 | Le Bras-Roulier et al. |
| 6,350,436 B1 | | 2/2002 | Glandorf et al. |
| 6,350,438 B1 | * | 2/2002 | Witt et al. .................... 424/53 |
| 6,355,229 B1 | | 3/2002 | Adamy |
| 6,440,395 B1 | | 8/2002 | Libin |
| 6,521,216 B1 | | 2/2003 | Glandorf et al. |
| 6,555,094 B1 | | 4/2003 | Glandorf et al. |
| 6,667,027 B2 | | 12/2003 | Glandorf et al. |
| 6,713,049 B1 | | 3/2004 | White, Jr. et al. |
| 6,746,681 B1 | | 6/2004 | Carroll |
| 6,814,958 B1 | | 11/2004 | Sekimoto |
| 6,821,507 B2 | | 11/2004 | Glandorf et al. |
| 6,846,478 B1 | * | 1/2005 | Doyle et al. .................... 424/49 |
| 2002/0068039 A1 | | 6/2002 | Pan et al. |
| 2002/0137728 A1 | | 9/2002 | Montgomery |
| 2003/0003061 A1 | | 1/2003 | Yue et al. |
| 2003/0035779 A1 | | 2/2003 | Brown et al. |
| 2003/0124067 A1 | | 7/2003 | Yue et al. |
| 2003/0198604 A1 | | 10/2003 | Lawlor |
| 2003/0206874 A1 | | 11/2003 | Doyle et al. |
| 2004/0126334 A1 | | 7/2004 | White et al. |
| 2005/0112070 A1 | | 5/2005 | Glandorf et al. |
| 2005/0163727 A1 | | 7/2005 | Doyle et al. |
| 2006/0034782 A1 | | 2/2006 | Brown et al. |

FOREIGN PATENT DOCUMENTS

| | | |
|---|---|---|
| WO | WO 94/18939 A1 | 9/1994 |
| WO | WO 94/27566 A1 | 12/1994 |
| WO | WO 96/15770 A1 | 5/1996 |
| WO | WO 97/16159 | 5/1997 |
| WO | WO 97/47292 | 12/1997 |
| WO | WO 98/08814 | 3/1998 |
| WO | WO 98/08815 | 3/1998 |
| WO | WO 98/08822 | 3/1998 |
| WO | WO 98/08823 | 3/1998 |
| WO | WO 98/08825 | 3/1998 |
| WO | WO 98/17195 | 4/1998 |
| WO | WO 98/17237 | 4/1998 |
| WO | WO 98/17270 | 4/1998 |
| WO | WO 99/06340 | 2/1999 |
| WO | WO 00/44338 A1 | 8/2000 |
| WO | WO 01/17494 | 3/2001 |
| WO | WO 03/075865 A1 | 9/2003 |
| WO | WO 2004/009105 A1 | 1/2004 |

OTHER PUBLICATIONS

Deriso, A.J., et al., "Chlorhexidine Gluconate 0.12% Oral Rinse Reduces the Incidence of Total Nosocmial Respiratory Infection and Nonprophylactic Systemic Antibiotic Use in Patients Undergoing Heart Surgery," Chest, Jun. 1996, pp. 1556-1561, vol. 109.

Grossi, S.G., et al., "Treatment of Periodontal Disease in Diabetics Reduces Glycated Hemoglobin," Journal of Periodontology, Aug. 1997, pp. 713-719., vol. 68.

Limeback, H., "Implication of Oral Infections on Systemic Diseases in the Instituionalized Elderly with a Special Focus on Pneumonia," Annals of Periodontology, Jul. 1998, pp. 162-175, vol. e.

Miller, L. S., et al., "The Relationships Between Reduction in Periodontal Inflammation and Diabetes Control: A Report of 9 Cases," Journal of Periodontology, Oct. 1992, pp. 843-848, vol. 63.

Williams, R. C., et al., Periodontology 2000, vol. 23, Jun. 2000, pp. 9-12, vol. 23.

* cited by examiner

ORAL CARE COMPOSITIONS CONTAINING COMBINATIONS OF ANTI-BACTERIAL AND HOST-RESPONSE MODULATING AGENTS

CROSS REFERENCE TO RELATED APPLICATION

This application is a continuation-in-part of application Ser. No. 09/607,602, filed Jun. 30, 2000, now abandoned.

FIELD OF THE INVENTION

The present invention relates to oral care compositions comprising combinations of therapeutic agents, specifically antibacterial agents combined with host-response modulating agents, in particular agents with anti-inflammatory activity for highly effective treatment and control of periodontal disease and for promotion of overall oral health and whole body or systemic health. The present compositions are particularly effective in inhibiting or killing bacterial pathogens in the oral cavity and in modulating host reaction to the presence of these pathogens and the toxins, endotoxins, inflammatory cytokines and mediators released by or prompted by these pathogens. By effectively treating and preventing periodontal disease, the present compositions also provide benefits to whole body or systemic health since periodontal infection is a risk factor in the development of a number of systemic conditions, including cardiovascular disease, stroke, atherosclerosis, diabetes, severe respiratory infections, premature births and low birth weight.

BACKGROUND OF THE INVENTION

Recent research has revealed that periodontal disease (gum disease) may be a far more serious threat to overall systemic health than previously realized. Periodontitis, a form of periodontal disease, is a tissue destructive process resulting from the accumulation of pathogenic bacteria along the gingival margin and the consequent tissue destructive host response to these pathogens. The presence of periodontitis can also result in the release of bacteria and/or bacterial toxins into the bloodstream. The host responses to the presence of these bacterial pathogens and/or toxins in the bloodstream may contribute to the development of atherosclerosis (heart disease), increase the risk of premature, underweight babies; and pose a serious threat to people whose health is compromised by diabetes, severe respiratory diseases, stroke and bacteremia (bacteria in the blood).

For a long time, it has been known that bacteria may affect the heart. Now evidence is mounting that suggests people with periodontitis, a bacteria-mediated disease, may be more at risk for heart disease, and have a significantly higher risk of having a fatal heart attack, than patients without periodontitis. Heart disease is the leading cause of death in most developed countries, and periodontitis is one of the most common bacterial-mediated diseases in humans, affecting as many as one third of those over 50. Thus even if periodontitis has only a modest effect on increasing the risk of heart attack, its prevalence may make it a significant contributor to the risk for heart disease in the population as a whole.

Several theories exist to explain the link between periodontal disease and heart disease. One theory is that oral bacterial pathogens enter the blood through inflamed gums, attach to fatty plaques in the coronary arteries (heart blood vessels) and cause small blood clots that contribute to clogged arteries. Researchers have found that 70% of the fatty plaque that blocks carotid arteries and causes stroke contains bacteria. Forty percent of those bacteria have been traced to the mouth. Coronary artery disease is characterized by a thickening of the walls of the coronary arteries due to the buildup of fatty proteins. Blood clots can obstruct normal blood flow, restricting the amount of nutrients and oxygen required for the heart to function properly. This may lead to heart attacks. Another possibility is that changes in systemic inflammatory mediators caused by periodontitis increase development of atherosclerotic plaque, which then contributes to thickening of the arterial walls.

Research also suggests that people with diabetes are more likely to have periodontitis than people without diabetes, and the presence of periodontitis may make it more difficult for diabetics to control their blood sugar. It is known that the presence of periodontitis can increase blood sugar, contributing to increased periods of time when the body functions with a high blood sugar level, which puts a diabetic person at increased risk for diabetic complications. Thus, controlling periodontitis may help control diabetes. A recent study ("Heightened Gingival Inflammation and Attachment Loss in Type 2 Diabetics with Hyperlipidemia," in *Journal of Periodontology*, November, 1999) found that poorly controlled type 2 diabetic patients are more likely to develop periodontal disease than well-controlled diabetics. The study further explains why diabetics are more susceptible to severe periodontal disease. The study concluded that poorly controlled diabetics respond differently to bacterial plaque at the gum line than well-controlled diabetics and non-diabetics, possibly due to elevated serum triglycerides. Poorly controlled diabetics have more harmful proteins (cytokines) in their gingival tissue, causing destructive inflammation of the gums. In turn beneficial proteins (growth factors) are reduced, interfering with the healing response to infection. "Increased serum triglyceride levels in uncontrolled diabetics seem to be related to greater attachment loss and probing depths, which are measures of periodontal disease," said Christopher Cutler, D.D.S., Ph.D., the study's lead researcher.

Evidence is also mounting that suggests pregnant women who have periodontitis may be significantly more likely to have a premature, low-birthweight baby. The inflammatory response prompted by periodontitis and/or the associated presence of bacterial pathogens/toxins in the bloodstream are cause for concern among pregnant women because they pose a risk to the health of the fetus. The presence of periodontitis appears to retard fetal growth by releasing into the woman's bloodstream bacterial toxins that reach the placenta and interfere with fetal development by increasing systemic levels of inflammatory mediators that could prompt pre-term birth. Scientists have also proposed that the presence of a low-grade infection may influence harmed cells to discharge inflammatory chemicals, similar to those used to induce abortion. This can cause the cervix to dilate and set off uterine contractions. The risk of having a premature baby of low birth weight was estimated to be at least 7.5 times as high for women with severe periodontal disease, and to occur in 5 percent of pregnancies, costing the U.S. $5.7 billion a year. [S. Offenbacher, *J. Periodontol.* 1996 October; 67(10 Suppl): 1103-13].

Research further suggests that periodontal disease may pose an increased risk for severe respiratory diseases like pneumonia, bronchitis, emphysema and chronic obstructive pulmonary disease.

The VA Dental Longitudinal Study (DLS) and Normative Aging Study (NAS) examined the relationship of periodontal disease to mortality from all outcomes and concluded that periodontal status at baseline was a significant and independent predictor of mortality. [*Annals of Periodontology*, 3(1), 339-49, July 1998] The study was conducted starting in the mid-1960s among men on good medical health and followed over more than a 25-year period. It was found that for each 20% increment in mean whole-mouth ABL (alveolar bone loss, measured with a Schei ruler using full-mouth series of periapical films), the subject's risk of death increased by 51%. The risk of death was also found to be associated with periodontal status as measured clinically by periodontal probing depth. Subjects in the population group with the deepest average probing depths were found to be at 74% higher risk.

According to Dr. Michael Roizen, University of Chicago internist and anesthesiologist, keeping teeth and gums healthy adds 6.4 years to a person's life. Indeed, the American Academy of Periodontology (AAP) concurs that keeping teeth and gums healthy is as significant as taking vitamins, quitting smoking and reducing stress as among the top things that a person can do to add years to life.

Periodontal disease ("gum disease") is a broad term used to describe those diseases which attack the gingiva and the underlying alveolar bone supporting the teeth. The disease exists in a number of species of warm blooded animals such as humans and canines, and includes a series of diseases exhibiting various syndromes which vary from each other according to the stage or situation of the disease or the age of the patient. The term is used for any inflammatory disease which initially occurs at a marginal gingiva area and may affect the alveolar bone. Periodontal disease affects the periodontium, which is the investing and supporting tissue surrounding a tooth (i.e., the periodontal ligament, the gingiva, and the alveolar bone). Two common stages of periodontal disease are gingivitis (inflammation of the gingiva) and periodontitis (inflammation of the periodontal ligament manifested by progressive resorption of alveolar bone, increasing mobility of the teeth, and loss of the teeth at advanced stage). Combinations of inflammatory and degenerative conditions are termed periodontitis complex. Other terms used for various aspects of periodontal disease are "juvenile periodontitis", "acute necrotizing ulcerative gingivitis", and "alveolar pyorrhea".

Periodontal disease may involve one or more of the following conditions: inflammation of the gingiva, formation of periodontal pockets, bleeding and/or pus discharge from the periodontal pockets, resorption of alveolar bone, loose teeth and loss of teeth. Bacteria present in dental plaque which forms on the surface of the teeth and in the periodontal pocket contribute to both the initiation and progress of periodontal disease. Thus, in order to prevent or treat periodontal disease, these bacteria must be suppressed by some means other than simple mechanical scrubbing. Towards this end, there has been a great deal of research aimed at developing therapeutic dentifrices, mouthwashes, and methods of treating periodontal disease, which are effective in suppressing these bacteria. However, periodontal disease involves more than the bacterial infection. Severe periodontal disease involves the destruction of periodontal tissue, which is primarily caused by the indirect effects mediated by the host's reaction to the bacteria in the periodontium and gingival sulcus, specifically inflammation.

As indicated, gingivitis is an inflammatory disease of the gingival and periodontium characterized by redness, swelling and bleeding upon probing. If left unchecked, gingivitis may progress into periodontitis, which may result in attachment loss, bone destruction and tooth loss. Anaerobic bacteria are generally regarded as the initiating agent of gingivitis, with subsequent progression and disease severity determined by the host immune response, i.e., inflammation, which is a nonspecific cellular and biochemical process involving multiple pro-inflammatory agents.

Bacterial metabolites induce leukocyte chemotaxis which results in the accumulation of inflammatory cells at the site of the bacterial challenge. Furthermore, bacterial metabolites induce the production of inflammatory mediators by leukocytic cells, in particular monocytes. Amongst these are local disease mediators such as metabolites of arachidonic acid, e.g. leukotrienes, prostaglandins and thromboxanes. Prostaglandins have been found to be particularly important in the metabolism and destruction of tissue and alveolar bone. Indeed, the production of prostaglandins in the periodontal tissues has been found to be an important mediator of the loss of alveolar bone in the periodontium. Patients with periodontal breakdown show an elevated prostaglandin $E_2$ level both in the gingival tissue as well as in the crevicular fluid. Prostaglandins and thromboxanes are formed from arachidonic acid by an enzyme cascade, the first step of which is the cyclooxygenation by an enzyme called cyclooxygenase (COX). Inhibiting the cyclooxygenase would inhibit the formation of prostaglandins and thus reduce alveolar bone loss, and indeed certain cyclooxygenase inhibitors, particularly non steroidal anti-inflammatory drugs such as indomethacin and flurbiprofen have been found to markedly reduce the resorption of alveolar bone.

Once inflammation starts, the process can self-propagate even when the causative agent is removed. Therefore, an anti-bacterial, such as stannous, zinc, CPC and peroxide, in combination with an anti-inflammatory agent would be a more effective therapy for gingivitis than the conventional method of using anti-bacterial agents alone. The present invention involves such combination of particular anti-bacterial agents and anti-inflammatory agents in oral care compositions to effectively treat and prevent bacteria-mediated diseases of the oral cavity and thereby inhibit periodontal bacteria-induced systemic disease.

SUMMARY OF THE INVENTION

The present invention encompasses oral care compositions comprising the combination of particular antibacterial agents with agents having anti-inflammatory activity, i.e., against one or more of inflammatory factors produced by the body (host) in response to bacterial infection in the oral cavity, including matrix metalloproteinases (MMP's), cyclooxygenases (COX), $PGE_2$, interleukin 1 (IL-1), IL-1β converting enzyme (ICE), transforming growth factor β1 (TGF-β1), inducible nitric oxide synthase (iNOS), hyaluronidase, cathepsins, nuclear factor kappa B (NF-κB), and IL-1 Receptor Associated Kinase (IRAK) to provide enhanced efficacy against bacteria-mediated diseases of the oral cavity. The present compositions are effective in inhibiting and/or killing pathogenic oral bacteria and in modulating host reaction to the presence of these pathogens in the oral cavity as well as to the toxins, endotoxins, inflammatory cytokines and mediators released by or prompted by these pathogens.

DETAILED DESCRIPTION OF THE INVENTION

The present invention involves topical oral care compositions comprising the combination of an anti-bacterial agent with an anti-inflammatory agent in an orally acceptable carrier for effective treatment and prevention of bacteria-mediated diseases and conditions in the oral cavity and for modulating host reaction to bacterial pathogens present in the oral cavity and to the toxins, endotoxins, inflammatory cytokines and mediators associated therewith. The present invention also encompasses methods of use of these compositions comprising topical application to the oral cavity. The benefits of the present compositions and methods extend beyond treating and preventing oral bacterial infections in the oral cavity to promoting whole body or systemic health.

By "whole body health" as used herein is meant overall systemic health characterized by a reduction in risk of development of major systemic diseases and conditions including cardiovascular disease, stroke, diabetes, severe respiratory infections, premature births and low birth weights (including post-partum dysfunction in neurologic/developmental function), and associated increased risk of mortality.

The term "diseases and conditions of the oral cavity," as used herein, includes periodontal disease, gingivitis, periodontitis, periodontosis, adult and juvenile periodontitis, and other inflammatory conditions of the tissues within the oral cavity, plus caries, necrotizing ulcerative gingivitis, resulting conditions from these diseases such as oral or breath malodor, and other conditions such as herpetic lesions, and infections that may develop following dental procedures such as osseous surgery, tooth extraction, periodontal flap surgery, dental implantation, and scaling and root planing. Also specifically included are dentoalveolar infections, dental abscesses (e.g., cellulitis of the jaw; osteomyelitis of the jaw), acute necrotizing ulcerative gingivitis (i.e., Vincent's infection), infectious stomatitis (i.e., acute inflammation of the buccal mucosa), and Noma (i.e., gangrenous stomatitis or cancrum oris). Oral and dental infections are more fully disclosed in Finegold, *Anaerobic Bacteria* in *Human Diseases*, chapter 4, pp 78-104, and chapter 6, pp 115-154 (Academic Press, Inc., NY, 1977. The compositions and methods of treatment of the present invention are particularly effective for treating or preventing periodontal disease (gingivitis and/or periodontitis) and breath malodor.

By "topical oral composition" or "oral care composition" as used herein means a product which in the ordinary course of usage is not intentionally swallowed for purposes of systemic administration of particular therapeutic agents, but is rather retained in the oral cavity for a time sufficient to contact substantially all of the dental surfaces and/or oral tissues for purposes of oral activity.

The topical oral composition of the present invention may be in various forms including toothpaste, dentifrice, tooth powder, topical oral gel, mouthrinse, denture product, mouthspray, mousse, foam, lozenge, oral tablet, and chewing gum.

The term "dentifrice", as used herein, means paste, gel, or liquid formulations unless otherwise specified. The dentifrice composition may be in any desired form, such as deep striped, surface striped, multi-layered, having the gel surrounding the paste, or any combination thereof.

By "safe and effective amount" as used herein means sufficient amount of active agent to provide the desired benefit while being safe to the hard and soft tissues of the oral cavity. The safe and effective amount of anti-bacterial agent or anti-inflammatory agent, will vary with the particular condition being treated, the age and physical condition of the patient being treated, the severity of the condition, the duration of treatment, the nature of concurrent therapy, the specific form of the agent(s) employed, and the particular vehicle from which the agent(s) are applied.

The term "orally acceptable carrier" as used herein includes safe and effective materials for use in the compositions of the present invention. Such materials are conventional additives in oral care compositions including but not limited to fluoride ion sources, anti-calculus or anti-tartar agents, buffers, abrasives such as silica, bleaching agents such as peroxide sources, alkali metal bicarbonate salts, thickening materials, humectants, water, surfactants, titanium dioxide, flavor system, sweetening agents, xylitol, coloring agents, and mixtures thereof.

Herein, the terms "tartar" and "calculus" are used interchangeably and refer to mineralized dental plaque biofilms.

All percentages used herein are by weight of the oral care composition, unless otherwise specified. The ratios used herein are molar ratios of the overall composition, unless otherwise specified. All measurements are made at 25° C., unless otherwise specified.

Herein, "comprising" and its variants mean that other steps and other ingredients which do not affect the end result can be added. The terms encompass the terms "consisting of" and "consisting essentially of".

As used herein, the word "include," and variants, are intended to be non-limiting, such that recitation of items in a list is not to the exclusion of other like items that may also be useful in the materials, compositions, devices, and methods of this invention.

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Active and other ingredients useful herein may be categorized or described herein by their therapeutic and/or cosmetic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated application or applications listed.

The present compositions are used to treat and prevent diseases and conditions of the oral cavity including periodontal disease, thereby promoting and enhancing whole body or systemic health for the individual being treated, as evidenced by the following health indices (or biomarkers):

1) reduction in risk of development of heart attack, stroke, diabetes, severe respiratory infections, low birth weight infants, post-partum dysfunction in neurologic/developmental function, and associated increased risk of mortality;
2) reduction in the development of fatty arterial streaks, atherosclerotic plaques, progression of plaque development, thinning of the fibrous cap on atherosclerotic plaques, rupture of atherosclerotic plaques, and the subsequent blood clotting events;
3) reduction in carotid arterial (intimal) wall thickness (e.g., as assessed by ultra-sound techniques)
4) reduction in exposure of blood and systemic circulation to oral pathogens and/or their toxic components, specifically leading to reduction in blood levels of oral bacteria, lipopolysaccharide (LPS) and/or the incidence of oral pathogens and/or components thereof found in arterial plaques, arterial structures, and/or distant organs (e.g., heart, liver, pancreas, kidney);
5) reduction in the exposure of the lower respiratory track to the inhalation of bacterial pathogens and the subsequent development of pneumonias and/or exacerbation of chronic obstructive lung disease;
6) reduction in alterations in circulating hematocrit, hemoglobin, white blood cell count and/or platelet counts;

7) reduction in the incidence of disregulation in blood/serum and saliva levels of inflammatory mediators/cytokines such as TNF-α, IL-1, IL-6, and CD-14;
8) reduction in the incidence of disregulation of blood/serum and saliva levels of acute phase reactants including C-reactive protein, fibrinogen, α1-antitrypsin, and haptoglobin;
9) reduction in the incidence of disregulation of blood/serum and saliva markers of metabolic disregulation including homocysteine, glycosylated hemoglobin, 8-iso-PGF-2alpha, and uric acid;
10) reduction in incidence of disregulation of glucose metabolism as typically assessed by impaired glucose tolerance test, increased fasting blood glucose levels, and abnormal fasting insulin levels; and
11) reduction in disregulation of blood lipid levels including blood or serum cholesterol, triglycerides, LDL, HDL, VLDL, Apolipoprotein B, and/or Apolipoprotein A-1.

Without wishing to be bound by theory, it is believed that the present compositions promote whole body or systemic health by effectively modulating the body's response to pathogenic oral bacteria and associated bacterial toxins, endotoxins, inflammatory mediators and cytokines. The present compositions are effective in treating and preventing bacteria-mediated diseases present in the oral cavity, including plaque, gingivitis, periodontitis, and herpetic lesions, as well as infections that may develop following dental procedures such as osseous surgery, tooth extraction, periodontal flap surgery, dental implantation, and scaling and root planing. By controlling bacteria-mediated diseases and conditions present in the oral cavity, spread into the bloodstream and other parts of the body of pathogenic bacteria and associated harmful substances including toxins and endotoxins is prevented or minimized.

Oral infections can lead to systemic infection. Bacteria can spread from the mouth into the bloodstream and other parts of the body, putting a person's health at risk. Recent research has found that periodontitis may contribute to the development of a number of serious conditions including heart disease, diabetes, severe respiratory diseases and premature, underweight births.

It is now known that chronic oral cavity infection produces a biologic burden of bacterial toxins and inflammatory cytokines that may initiate and exacerbate atherosclerosis and thromboembolic events. Additionally, a known periodontal pathogen, *Porphyromonas gingivalis* has been isolated from arteriosclerotic plaques. Periodontal disease has also been shown to induce episodes of significant bacteremias and thromboembolic events such as myocardial infarction; stroke can occur following bacteremia. Certain bacteria associated with oral cavity diseases, *Streptococcus sanguis* and *Porphyromonas gingivalis*, have been demonstrated to cause platelets to aggreggate upon contact with these bacteria. The resultant bacterially-induced platelet aggregates can form the emboli which are responsible for the acute myocardial infarction or stroke.

Periodontitis, a common form of periodontal disease, is believed to be caused by a small group of Gram-negative bacteria present on the tooth root surfaces as biofilms. Biofilms are defined as matrix-enclosed bacterial populations adherent to each other and/or to surfaces or interfaces. Experts have recently concluded that three species, all of which are Gram-negative and anaerobic, are present in these biofilms and account for most cases of periodontitis. These are *Porphyromonas gingivalis, Bacteroides forsythus* and *Actinobacillus actinomycetemcomitans*, with the latter found mostly in cases of juvenile periodontitis. The bacteria in the biofilms shed vesicles that are rich in lipopolysaccharides (LPS). Bacteria and bacterial substances, especially LPS, traverse the junctional and pocket epithelium to gain access to connective tissue and blood vessels, initiate and perpetuate immunoinflammation. All of the components of blood and serum pass into the connective tissue. B- and T-lymphocytes, plasma cells and macrophages appear in the periodontal tissues. LPS interacts with monocytes and macrophages to activate cells to synthesize large quantities of pro-inflammatory cytokines (including IL-1, TNFα, $PGE_2$) and matrix metalloproteinases (MMP's). MMP's destroy the connective tissues of the gingiva and periodontal ligament; IL-1, TNFα, and $PGE_2$ have been shown to mediate bone destruction. Periodontitis may enhance susceptibility to systemic diseases in several ways. LPS and viable Gram-negative bacteria from the biofilms and cytokines from inflamed periodontal tissues may enter the circulation in pathogenic quantities.

In one aspect the present invention relates to topical oral compositions for humans and animals, including therapeutic rinses, especially mouth rinses; dentifrices such as toothpastes, tooth gels, and tooth powders; non-abrasive gels; mouth sprays; mousse; foams; chewing gums, lozenges and breath mints; dental solutions and irrigation fluids; dental implements such as dental floss and tape; and pet care products including nutritional supplements, food, drinking water additives, chews or toys, comprising a combination of (a) one or more of a first active agent having inhibitory activity against at least one of host pro-inflammatory factors selected from matrix metalloproteinases (MMP's), cyclooxygenases (COX), $PGE_2$, interleukin 1 (IL-1), IL-1β converting enzyme (ICE), transforming growth factor β1 (TGF-β1), inducible nitric oxide synthase (iNOS), hyaluronidase, cathepsins, nuclear factor kappa B (NF-κB), and IL-1 Receptor Associated Kinase (IRAK); and (b) one or more of a second active agent having inhibitory activity against at least one of bacterial virulence factors selected from biofilm formation, biofilm adherence and bacterial enzymes selected from gingipains, METase, and Cystalysin.

The combination of at least two different active agents provides enhanced efficacy to treat and prevent bacteria-mediated oral cavity conditions and to inhibit oral-bacteria-mediated systemic diseases.

The first active agent has anti-inflammatory activity as demonstrated by activity against at least one, preferably two or more of key host pro-inflammatory factors including matrix metalloproteinases (MMP's), cyclooxygenases (COX), $PGE_2$, interleukin 1 (IL-1), IL-1β converting enzyme (ICE), transforming growth factor β1 (TGF-β1), inducible nitric oxide synthase (iNOS), hyaluronidase, cathepsins, nuclear factor kappa B (NF-κB), and IL-1 Receptor Associated Kinase (IRAK). Elevated levels of these factors are associated with gingivitis and periodontitis, indicating these components are major mediators of inflammation in the host.

MMP's (including various subtypes, e.g., MMP 1, 2, 3, 8, 9, 13), are host extracellular matrix proteases that contribute to tissue destruction and remodeling. COX enzymes catalyze the conversion of arachidonic acid into prostaglandins, which result in vasodilation, redness, puffiness and pain. IL-1β is a pro-inflammatory cytokine which induces the synthesis of $PGE_2$ and various MMP's and is likely involved in destruction of alveolar bone. IL-1β is synthesized as a larger precursor peptide and requires the cleavage by ICE into the active form. ICE is thus the processing enzyme for the production of IL-1β. IRAK's are signaling molecules downstream from IL-1β. Inducible nitric oxide synthase (iNOS) is an enzyme involved in the production of large amounts of nitric oxide, which may be cytotoxic. TGF-β1 promotes cellular proliferation and is suggested to be one of the growth factors modulating exaggerated host response together other major mediators of inflammation. Hyaluronidase catalyzes the degradation of endogenous hyaluronic acid (hyaluronan), a glycosaminoglycan with anti-inflammatory and antiedematous properties, thus having a beneficial effect on plaque-induced gingivitis. Inhibiting hyaluronidase would thus increase the endogenous level of hyaluronic acid. A major feature of gingivitis and periodontitis is the destruction of the collagenous matrix of the surrounding connective tissue. Cathepsins are proteolytic enzymes released from cells adjacent to the site of destruction. Nuclear factor-kappa B (NF-κB) is a transcriptional factor that is stimulated by LPS and stimulates the expression of multiple cytokines and MMP's, thus controlling multiple inflammatory pathways.

Because inflammation in itself is a multi-factorial process, preferred anti-inflammatory agents are those that suppress at least two different pro-inflammatory factors. Even more effective are agents that suppress three or more of these pro-inflammatory factors. Or combinations of agents may be used to complement each other and provide activity against multiple, preferably most or all pro-inflammatory factors.

The activity of potential agents was tested in terms of their ability to inhibit purified host and bacterial enzymes known to be involved in gingivitis and periodontitis. The inhibition of purified human MMP's (supplied by Biomol International) and ICE (supplied by Calbiochem) was measured by the cleavage of the fluorogenic substrates Mca-Pro-Leu-Gly-Leu-Dpa-Ala-Arg-$NH_2$ (Biomol International) and N-acetyl-Trp-Glu-His-Asp-AMC (Biomol International), respectively. Activity was measured using a fluorescence assay described in C. G. Knight, et al. *FEBS Lett.* 296, 263 (1992).

The inhibition of cyclooxygenases COX1 and 2 was measured using the Cayman COX Screening Assay Kit (Cayman Chemical) according to manufacturer's instructions.

TGF-β activity was measured using a β-lactamase reporter gene under the control of the Smad Binding Element (SBE) expressed in human embryonic kidney HEK 293 cells. The inhibiton of TGF-β activity was monitored by a decrease of TGF-β-induced β-lactamase activity. β-lactamase activity was measured by the cleavage of a fluorogenic substrate containing two fluoroprobes (coumarin and fluorescein) using a fluorescence resonance energy transfer assay.

IL-1R (receptor) activity was measured using a gene reporter assay in human endothelial ECV 304 cells. The reporter gene ICAM-1/luciferase is under the control of the ICAM-1 promoter regulated by two transcriptional factors NF-κB and AP-1, which are activated by IL-1R. The inhibiton of IL-1R activity was monitored by a decrease of IL-1β-induced luciferase activity. Luciferase activity was measured using an ATP-dependent chemiluminescence assay.

Inhibition of $PGE_2$ formation was measured by the reduction in IL-1β-induced-$PGE_2$ release in human epithelial A549 cells. The amount of $PGE_2$ released into the tissue culture was measured using the $PGE_2$ Homogeneous Time Resolved Fluorescence (HTRF) kit (supplied by CisBio) according to manufacturer's instructions.

The assays identified agents having anti-inflammatory activity including vitamin compounds such as riboflavin, riboflavin phosphate, folic acid, cyanocobalamin (vitamin B12), and menadione (vitamin K3); curcuminoids such as curcumin, demethoxycurcumin, bismethoxycurcumin and tetrahydrocurcumin; oils and extracts from spices and botanicals such as clove, cinnamon, cassia, ginger, basil, coriander, cilantro and allspice which contain active compounds including cinnamaldehyde, cinnamic acid, guaiacol and derivatives such as eugenol, isoeugenol, dihydroeugenol, vanillyl butyl ether, vanillin (4-formyl-guaiacol), 5-propenylguaethol, 4-ethyl-2-methoxyphenol, 4-allyl-2-methoxyphenol acetate, and 4-methyl guaiacol; oils or extracts of thyme, oregano and sage containing thymol, carvacrol and carvacryl ethyl ether; neem oil; flavonoids and flavones such as baicalein, baicalin, wogonoside, wogonin, and quercetin; phenolics from plant sources such as tea and cranberry including catechin, gallo-catechin gallate, epicatechin (EC), epigallocatechin (EGC), epigallocatechin gallate (EGCG), epicatechin gailate (ECG), theaflavine, thearubigins, anthocyanidins/proanthocyanidins and anthocyanins (e.g., cyanidin, delphinidin, pelargonidin, peonidin, malvidin and petunidin); tannic acid; gallic acid; ellagic acid; ellagitannins; hexamidine; and berberine.

Results of assays demonstrating the activity of representative useful agents are summarized in Table 1 below. Where no data are reported is not an indication that the compound/active has no activity; rather that the compound/active was not tested for that activity.

TABLE I

Inhibition of Host Pro-Inflammatory Factors

| Active | MMP-1 | MMP-2 | MMP-3 | MMP-9 | MMP-13 | COX-1 | COX-2 | $PGE_2$ | IL-1 | TGF-β1 | ICE |
|---|---|---|---|---|---|---|---|---|---|---|---|
| Riboflavin | ++++ | ++++ | ++++ | ++ | ++ | ++++ | ++++ | + |  |  | ++++ |
| Baicalein | ++++ | ++++ | +++ | +++ |  | ++++ | ++++ | ++++ | + | ++ |  |
| Tannic Acid | + | ++ | + | + | + | ++++ | ++++ | ++++ | + | + |  |
| Quercetin | + | ++ | + | + |  | ++++ | ++++ | ++++ | +++ | +++ |  |
| Thymol | + | + | + | + |  | ++++ | ++++ | ++++ | + | + |  |
| Folic Acid | + | +++ | + | ++++ |  | ++++ | ++++ | + | + | + |  |
| Hexamidine | + | + | + | ++++ |  |  |  | ++++ |  |  | + |
| Epigallocatechin |  | +++ |  |  |  | ++++ | ++++ |  |  |  |  |
| EGCG |  | +++ |  |  |  | ++++ | +++ | ++++ | + | ++ |  |
| Eugenol |  | + | + |  |  | ++ | ++ | ++++ | + | + |  |
| Dihydroeugenol |  | + | + |  |  | ++++ | ++++ | ++++ | + | ++ |  |
| Curcumin |  | +++ |  |  |  |  |  | ++++ | ++++ |  |  |
| Cinnamaldehyde |  | + | ++ |  |  | + | + | ++++ | + | + |  |
| Carvacrol |  | + | + |  |  | +++ | ++ | ++++ | + | + |  |
| Berberine |  |  |  |  |  | ++++ | + | ++ |  |  |  |
| Anthocyanidine |  |  | + |  |  |  |  | ++ |  |  |  |
| Clove Oil |  |  |  |  |  | ++++ | ++++ |  |  | + |  |
| Ginger Oleoresin |  |  | + |  |  |  |  | ++++ |  |  |  |
| Parsley Seed Oleoresin |  |  | + |  |  |  |  | ++++ |  |  |  |

TABLE I-continued

Inhibition of Host Pro-Inflammatory Factors

| Active | MMP-1 | MMP-2 | MMP-3 | MMP-9 | MMP-13 | COX-1 | COX-2 | PGE$_2$ | IL-1 | TGF-β1 | ICE |
|---|---|---|---|---|---|---|---|---|---|---|---|
| Coriander Oleoresin | | | + | | | | ++++ | | | | |
| Sage Oil | | | + | | | | ++++ | | | | |
| Basil Oil | | | + | | | | ++++ | | | | |
| Allspice | | | + | | | | ++++ | | | | |
| CPC | ++++ | ++ | ++++ | ++++ | ++++ | ++++ | +++ | +++ | +++ | + | + |
| SnF$_2$ | + | ++ | ++ | ++ | ++ | | | | | | + |
| Zinc Citrate | +++ | ++++ | ++ | +++ | + | | | | | | ++++ |
| Zinc Lactate | +++ | +++ | ++ | +++ | +++ | | | | | | ++++ |
| Zinc Oxide | + | +++ | + | ++ | + | + | + | + | + | + | ++++ |
| Triclosan | ++++ | + | ++++ | +++ | ++++ | + | + | ++ | ++ | +++ | + |
| Cu Gluconate | | + | ++ | | | + | + | + | + | + | |
| Cu Sulfate | | | + | | | + | + | + | ++ | + | |

+ % inhibition <25% at 200 uM
++ % inhibition ≧25% at 200 uM
+++ % inhibition ≧50% at 200 uM
++++ % inhibition ≧75% at 200 uM Additional useful agents that have been identified as having activity, for example, as inhibitor of MMP's, include menthyl anthranilate, (used commercially in lip balm as a sunscreen agent); hexyl isobutyrate (grape flavorant); 4-hydroxybenzaldehyde (flavor component of vanilla extract); a broad group of polyphenols including resveratrol (component of red wines, found in grape skins), isoliquertigenin (found in licorice), apigenin (found in chamomile), pratol (found in red clover), 4'-methoxyflavone, 8-methyl-4'-methoxyflavone and 6-methyl-4'-methoxyflavone. Additional agents with inhibitory activity include: brazilin and quercetin against iNOS; green tea and Echinacea extracts against hyaluronidase; cinnamon against cathepsins; curcumin, caffeic acid phenethyl ester, preparations of bee propolis, and silymarin against NF-κB; and curcumin, fisetin, quercetin, luteoline, apigenin and diosmetin against IRAK's. Additional agents with anti-inflammatory activity include a wide variety of plant-derived chemicals: flavonoids, isoflavonoids and other phenolics (e.g., myricetin, kaempferol, luteolin, hesperitin, naringenin, pterostilbene, rutin, rosmarinic acid, glabridin); carotenoids (e.g., lycopene, lutein, zeaxanthin, astazaxanthin, beta-carotene); limonoids and terpenoids (e.g., limonene, geraniol, farnesol); phytosterols (e.g., beta-sitosterol, stigmasterol, campesterol, ursolic acid); allicin; chlorogenic acid; ferulic acid; emodin; isothiocyanates (e.g., sulphoraphane); N-acetyl cysteine; phytic acid; and betaine.

One advantage of the present invention is that many of the most potent active agents are natural materials already known to be safe for ingestion. For example, a number of the polyphenols above that have potent anti-inflammatory activity are natural components of tea (*Camellia sinensis*) which are regularly consumed by humans. Some examples of teas suitable for providing tea polyphenols herein include but are not limited to, red tea, oolong tea, baozhong tea, hangzhou tea, and green tea. Furthermore, the present materials are not antibiotics but ameliorate the progress of periodontal disease without harming beneficial oral microbial flora. Tea polyphenols for instance have the ability to even enhance the growth of beneficial microbes (e.g., Bifidobacillus). Actives in practice today, such as chlorohexidine, doxycycline and metronidazole, are antibiotics with potential bacterial resistance issues along with a more widespread organism killing potential, i.e., both harmful and beneficial bacteria.

The antibacterial agents preferred in the present invention are those with selectivity for gram negative anaerobic bacteria involved in periodontal disease, such as *P. gingivalis, B. forsythus, A. actinomycetemcomitans, T. denticola, T. socranskii, F. nucleatum*, and *P. intermedia* and against other oral cavity strains such as *L. acidophilus, L. casei, A. viscosus, S. sobrinus, S sanguis, S. viridans*, and *S. mutans*. The present compositions are effective in killing, and/or altering bacterial metabolism, and/or suppressing the growth of, these microorganisms which cause topically-treatable infections and diseases of the oral cavity.

*P. gingivalis*, is a gram-negative anaerobe responsible for most periodontal disease in humans and companion animals. *P. gingivalis* infects the gingival sulcus, producing a number of virulence factors including cysteine proteases known as gingipains. Gingipains act on several immune system molecules, including kinogens, complement factors, immunoglobins, resulting in fluid influx into the sulcus, neutrophil recruitment, and bleeding. The ultimate result is a host inflammatory response characterized by COX2 induction, protease expression (MMP's), prostaglandin elevation and reactive oxygen elevations which result in tissue damage and bone resorption, eventually leading to tooth detachment. Inhibition of the proteolytic action of gingipains on immunoregulatory proteins should lead to a reduction in the inflammatory host-response and subsequent tissue damage. Antibacterial activity of oral care agents may thus be assessed in terms of their inhibitory activity against gingipains and other bacterial enzymes, for example, METase and Cystalysin, which are involved in degrading sulfur-containing amino acids to produce volatile sulfur compounds (VSC) such as hydrogen sulfide or methyl mercaptan that lead to bad breath or oral malodor.

The activity of R-gingipain was measured by the cleavage of the fluorogenic substrate Z-Phe-Arg-AMC.HCl (Calbiochem). Recombinant catalytic domain of R-gingipain of *Porphyromonas gingivalis* was expressed in and purified from *E. coli*. Activity of R-gingipain was measured by a fluorescence assay.

METase activity was measured by the conversion of L-methionine into ketobutyrate which is quantitated by coupling to a hydrazine, using a spectrophotometry method described in Takakura, et al. *Analytical Biochemistry* 327: 233-240 (2004). Cystalysin activity was measured by coupling pyruvate production to the reduction of NADH via lactate dehydrogenase.

Another aspect of antibacterial activity of the present agents relates to biofilm formation and dispersion or disruption. Biofilms form when microorganisms establish themselves on a surface and activate genes involved in producing a matrix that includes polysaccharides. This matrix may provide protection of biofilm bacteria from biocides. Molecules called quorum-sensing signals help trigger and coordinate part of the process of forming a biofilm. Bacteria constantly secrete low levels of the signals and sense them either through receptors on their surfaces, or internally. The receptors trigger behavioral changes when there are enough bacteria to allow the signals' concentrations to achieve a critical threshold. Once this occurs, bacteria respond by adopting communal behavior, such as forming a biofilm, and in the case of pathogenic bacteria, deploying virulence factors such as toxins. In addition to communicating with members of their own species, bacteria also conduct inter-species communications, such that a biofilm may contain more than one species of bacteria. Biofilms that adhere to teeth and oral surfaces lead to plaque and calculus and eventually periodontal disease and other oral cavity infections. Useful antibacterial agents are those which prevent bacterial adherence, colonization in the mouth and maturation into biofilms. The activity of agents to inhibit biofilm formation and/or to disperse biofilms is measured using assay methods such as described in commonly assigned WO 02/088298A1. Control of biofilms is determined by assaying the amount of biofilm resulting from treatment in the presence of a test compound as compared to the amount resulting from treatment in the absence of a test compound. A change in the amount of biofilm present as a result of a treatment may result from an effect on the exopolysaccharide matrix of biofilm or an effect on a microorganism within the biofilm, or an effect on the relationship therebetween. For example, biofilm formation or dispersion may be measured using crystal violet as a quantitative, total biofilm staining dye that stains both cells and extracellular polysaccharide.

The antibacterial agents that are particularly useful in the practice of the present invention are those that have demonstrated inhibitory activity against one or more of the above bacterial enzymes and/or biofilms. Preferred anti-bacterial agents are those with multiple inhibitory activities. Results of assays demonstrating the activity of representative useful agents are summarized in Table II below. Where no data are reported is not an indication that the compound/active has no activity; rather that the compound/active was not tested for that activity.

Suitable antibacterial agents include cetyl pyridinium chloride (CPC), stannous ion agent, zinc ion agent, copper ion agent, iron ion agent, triclosan, ascorbyl stearate; oleoyl sarcosine, dioctyl sulfosuccinate, alkyl sulfate and mixtures thereof.

In addition to their antibacterial activity, it has also been discovered that the selected antibacterial agents above have anti-inflammatory activity as demonstrated using the same assays for the anti-inflammatory agents. For example, CPC was demonstrated to inhibit several MMP subtypes, with a rank order of potency of MMP13>MMP1>MMP9>MMP3>MMP2. CPC also inhibited other host pro-inflammatory enzymes including cyclooxygenases COX1 and COX2 and interleukin converting enzyme (ICE). Stannous fluoride was also demonstrated to have activity, with a rank order of potency of MMP13>MMP3>MMP2>ICE>MMP9>MMP1. These findings indicate that the anti-gingivitis benefit of oral actives such as CPC and stannous is mediated in part by their anti-inflammatory action and prevention of tissue destruction in addition to their anti-bacterial action.

TABLE II

Inhibition of Bacterial Enzymes/Factors

| Active | R-gingipain | METase | Cystalysin | Biofilm Prevention | Biofilm Dispersion |
|---|---|---|---|---|---|
| CPC | +++ | + | + | ++ | ++ |
| $SnF_2$ | ++++ | + | + | | +++ |
| Zinc Citrate | ++++ | + | + | | |
| Zinc Lactate | ++++ | + | + | | |
| Zinc Oxide | +++ | + | + | + | |
| Copper Gluconate | ++++ | ++ | + | + | |
| Copper Sulfate | ++++ | | + | | |
| Iron Gluconate | ++++ | + | + | + | |
| Iron Ascorbate | ++++ | + | + | + | |
| Ascorbyl Stearate | ++++ | | | + | |
| Oleoyl Sarcosine | ++++ | | | + | |
| Alkyl Sulfate | ++++ | | | + | + |
| Dioctyl Sulfosuccinate | ++++ | | | + | |
| Triclosan | ++ | + | + | | ++ |
| Riboflavin | ++++ | + | + | ++ | + |
| Epigallocatechin | ++++ | ++ | +++ | + | |
| EGCG | +++ | ++ | +++ | +++ | |
| Vitamin B12 | ++++ | | | ++++ | ++ |
| Menadione (Vit. K) | ++++ | | | + | |
| Rosmarinic Acid | ++++ | | | | |
| Baicalein | ++ | | | | |
| Folic Acid | ++ | | | + | |
| Thymol | + | | | +++ | ++ |
| Berberine | | ++ | +++ | | ++ |
| Carvacrol | + | + | + | + | |
| Cinnamaldehyde | | + | + | + | |
| Eugenol | | + | + | ++ | |
| Dihydroeugenol | + | + | + | ++ | |

+ % inhibition <25% at 200 uM (biofilm prevention and dispersion tested at 390 uM)
++ % inhibition ≥25% at 200 uM (biofilm prevention and dispersion tested at 390 uM)
+++ % inhibition ≥50% at 200 uM (biofilm prevention and dispersion tested at 390 uM)
++++ % inhibition ≥75% at 200 uM (biofilm prevention and dispersion tested at 390 uM)

A further discovery is that the anti-inflammatory agents above also have some anti-bacterial activity as measured using the in vitro assays for inhibition of bacterial virulence factors. For example, riboflavin, riboflavin monosodium phosphate, epigallocatechin and epigallocatechin gallate (EGCG) were found to have strong inhibitory activity against gingipain, METase, cystalysin and biofilms. Significantly, the efficacy of these agents is confirmed in clinical testing. For example, in a mouse model, riboflavin monosodium phosphate at 10 mM in drinking water significantly reduced bone loss due to infection with *P. gingivalis* compared to a no treatment control. In a dog gingivitis model, twice daily rinsing with aqueous riboflavin monosodium phosphate (0.39% by weight) was directionally better than treatment with chlorhexidine (0.12% by weight) for reduction of bleeding sites, and comparable to the chlorhexidine treatment for gingivitis index and inflammation index.

Thus the combination of the present anti-bacterial and anti-inflammatory agents provide enhanced efficacy against periodontal disease and its many aspects, specifically, reduction in plaque, reduction in puffy, bleeding gums and gingival inflammation; reduction in pocket depth, halt to the progressive loss of alveolar bone and tooth attachment; improvement in bad breath; and importantly, reduction in systemic inflammation leading to better whole body or systemic health. Most preferred combinations include agents having activity against both bacterial and host factors. The antibacterial agent will typically be present at from about 0.01% to about 20% by weight of the composition and the anti-inflammatory agent at from about 0.001% to about 10% by weight.

Additional Therapeutic Agents

The present compositions may optionally comprise additional therapeutic agents to obtain an optimal effect. Thus, for example, the present compositions may comprise an additional agent such as antimicrobial/antiplaque agents, biofilm inhibiting agents, antibiotics; analgesics and local anesthetic agents; dentinal desensitizing agents; odor masking agents, and other host-response modulating agents.

Antimicrobial antiplaque agents may include, but are not limited to, chlorhexidine (Merck Index, no. 2090), alexidine (Merck Index, no. 222); hexetidine (Merck Index, no. 4624); sanguinarine (Merck Index, no. 8320); benzalkonium chloride (Merck Index, no. 1066); salicylanilide (Merck Index, no. 8299); domiphen bromide (Merck Index, no. 3411); tetradecylpyridinium chloride (TPC); N-tetradecyl-4-ethylpyridinium chloride (TDEPC); octenidine; delmopinol, octapinol, and other piperidino derivatives; nisin preparations; essential oils (including methyl salicylate, eucalyptol, menthol); metal ion sources, such as manganese and silver and analogs and salts of the above antimicrobial antiplaque agents. If present, the antimicrobial antiplaque agents generally comprise at least about 0.01% by weight of the compositions of the present invention.

Biofilm inhibiting agents may include furanones, cell wall lytic enzymes such as lysozyme, plaque matrix inhibitors such as dextranases and mutanases, and peptides such as bacteriocins; histatins, defensins and cecropins.

Other optional therapeutic agents include antibiotics such as augmentin, amoxicillin, tetracycline, doxycycline, minocycline, metronidazole, neomycin, kanamycin, or clindamycin; dentinal desensitizing agents such as strontium chloride (suitably as hexahydrate), strontium acetate (suitably as hemihydrate), potassium nitrate, potassium citrate, sodium citrate/Pluronic gel, stannous fluoride, and sodium fluoride; odor masking agents such as peppermint oil or chlorophyll; local anesthetic agents such as lidocaine or benzocaine; and nutritional agents such as amino acids, essential fats, and minerals.

Other types of host-response modulating agents that may be incorporated in the present compositions are described in the following paragraphs.

H-2 Antagonists

Histamine-2 (H-2 or H2) receptor antagonist compounds (H-2 antagonists) may be used in the oral care composition of the present invention. As used herein, selective H-2 antagonists are compounds that block H-2 receptors, but do not have meaningful activity in blocking histamine-1 (H-1 or H1) receptors. Selective H-2 antagonists stimulates the contraction of smooth muscle from various organs, such as the gut and bronchi; this effect can be suppressed by low concentrations of mepyramine—a typical antihistaminic drug. The pharmacological receptors involved in these mepyramine-sensitive histamine responses have been defined as H-1 receptors (Ash, A. S. F. & H. O. Schild, Brit. J. Pharmacol Chemother., Vol. 27 (1966), p. 427. Histamine also stimulates the secretion of acid by the stomach (Loew, E. R. & O. Chickering, Proc. Soc. Exp. Biol. Med., Vol. 48 (1941), p. 65), increases the heart rate (Trendelenburg, U., J. Pharmacol., Vol. 130 (1960), p. 450), and inhibits contractions in the rat uterus (Dews, P. B. & J. D. P. Graham, Brit. J. Pharmacol. Chemother., Vol. 1 (1946), p. 278); these actions cannot be antagonized by mepyramine and related drugs. The H-2 antagonists useful in the oral care compositions or substances are those that blockade the receptors involved in mepyramine-insensitive, non-H-1 (H-2), histamine responses, and do not blockade the receptors involved in mepyramine-sensitive histamine responses.

Selective H-2 antagonists are those compounds found to be H-2 antagonists through their performance in classical preclinical screening tests for H-2 antagonist function. Selective H-2 antagonists are identified as compounds which can be demonstrated to function as competitive or non-competitive inhibitors of histamine-mediated effects in those screening models specifically dependent upon H-2 receptor function, but to lack significant histamine antagonist activity in those screening models dependent upon H-1 receptor function. Specifically, this includes compounds that would be classified as described by Black, J. W., W. A. M. Duncan, C. J. Durant, C. R. Ganellin & E. M. Parsons, "Definition and Antagonism of Histamine H2-Receptors", Nature, Vol. 236 (Apr. 21, 1972), pp. 385-390 (Black), as H-2 antagonists if assessed as described by Black through testing with the guinea pig spontaneously beating right atria in vitro assay and the rat gastric acid secretion in vivo assay, but shown to lack in significant H-1 antagonist activity relative to H-2 antagonist activity, if assessed as described by Black with either the guinea pig ileum contraction in vitro assay or the rat stomach muscle contraction in vivo assay. Preferably selective H-2 antagonists demonstrate no significant H-1 activity at reasonable dosage levels in the above H-1 assays. Typical reasonable dosage level is the lowest dosage level at which 90% inhibition of histamine, preferably 99% inhibition of histamine, is achieved in the above H-2 assays.

Selective H-2 antagonists include compounds meeting the above criteria which are disclosed in U.S. Pat. Nos. 5,294,433 and 5,364,616 to Singer, et al., issued Mar. 15, 1994 and Nov. 15, 1994 respectively and assigned to Procter & Gamble, wherein the selective H-2 antagonist is preferably selected from the group consisting of cimetidine, etintidine, ranitidine, ICIA-5165, tiotidine, ORF-17578, lupitidine, donetidine, famotidine, roxatidine, pifatidine, lamtidine, BL-6548, BMY-25271, zaltidine, nizatidine, mifentidine, BMY-25368 (SKF-94482), BL-6341A, ICI-162846, Ramixotidine, Wy-45727, SR-58042, BMY-25405, loxtidine, DA-4634, bisfentidine, sufotidine, ebrotidine, HE-30-256, D-16637, FRG-8813, FRG-8701, impromidine, L-643728, and HB-408. Particularly preferred is cimetidine (SKF-92334), N-cyano-N'-methyl-N"-(2-(((5-methyl-1H-imidazol-4-yl)methyl)thio)ethyl)guanidine:

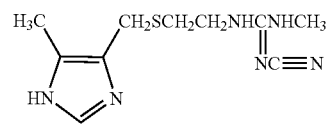

Cimetidine is also disclosed in the Merck Index, 11th edition (1989), p. 354 (entry no. 2279), and Physicians' Desk Reference, 46th edition (1992), p. 2228. Related preferred H-2 antagonists include burimamide and metiamide.

If present, the H-2 antagonist agents generally comprise from about 0.001% to about 20%, more preferably from about 0.01% to about 15%, more preferably still from about 0.1% to about 10%, still more preferably from about 1% to about 5%, by weight of the compositions of the present invention. In addition to cimetidine, preferred H-2 antagonists include ranitidine, famotidine, roxatidine, nizatidine and mifentidine.

Anti-Inflammatory Agents

Other anti-inflammatory agents may also be present in the oral compositions of the present invention. Such agents may include, but are not limited to, lipoxygenase inhibitors, such as nordihydroguaiaretic acid; cyclo-oxygenase inhibitors such as flurbiprofen; and non-steroidal anti-inflammatory agents such as aspirin, ketorolac, flurbiprofen, ibuprofen, naproxen, indomethacin, aspirin, ketoprofen, piroxicam and meclofenamic acid, rofecoxib, celecoxib, and mixtures thereof. If present, the other anti-inflammatory agents generally comprise from about 0.001% to about 5% by weight of the compositions of the present invention. Ketorolac is described in U.S. Pat. No. RE 036,419, issued Nov. 30, 1999; U.S. Pat. No. 5,785,951, issued Jul. 28, 1998 and U.S. Pat. No. 5,464,609, issued Nov. 7, 1995.

Matrix Metalloproteinase (MMP) Inhibitors

Other matrix metalloproteinase inhibitors may also be present in the oral compositions of the present invention. Metalloproteinases (MPs) are enzymes that often act on the intercellular matrix, and thus are involved in tissue breakdown and remodeling. Examples of MPs include human skin fibroblast collagenase, human skin fibroblast gelatinase, human sputum collagenase, aggrecanase and gelatinase, and human stromelysin. Collagenase, stromelysin, aggrecanase and related enzymes are thought to be important in mediating the symptomatology of a number of diseases including periodontal disease. Potential therapeutic indications of MP inhibitors have been discussed in the literature, including treatment of: rheumatoid arthritis (Mullins, D. E., et al., *Biochim. Biophys. Acta*. (1983) 695:117-214); osteoarthritis (Henderson, B., et al., *Drugs of the Future* (1990) 15:495-508); the metastasis of tumor cells (ibid, Broadhurst, M. J., et al., European Patent Application 276,436 (published 1987), Reich, R., et al., 48 *Cancer Res*. 3307-3312 (1988); and various ulcerations or ulcerative conditions of tissue. For example, ulcerative conditions can result in the cornea as the result of alkali burns or as a result of infection by *Pseudomonas aeruginosa, Acanthamoeba, Herpes simplex* and vaccinia viruses. Other examples of conditions characterized by undesired metalloproteinase activity include periodontal disease, epidermolysis bullosa, fever, inflammation and scleritis (DeCicco, et al., WO 95/29892 published Nov. 9, 1995).

Other MMP inhibitors useful for the present compositions may include, but are not limited to, hydroxamic acid derivatives, phosphinic acid amides, and heteroatom-containing cyclic and acyclic structures such as disclosed in U.S. Pat. No. 6,015,912, issued Jan. 18, 2000; U.S. Pat. No. 5,830,915, issued Nov. 3, 1998; U.S. Pat. No. 5,672,598, issued Sep. 30, 1997 and U.S. Pat. No. 5,639,746, issued Jun. 17, 1997 and in WO 99/52868; WO 99/06340; WO 98/08827; WO 98/08825; WO 98/08823; WO 98/08822; WO 98/08815; and WO 98/08814, all assigned to the Procter & Gamble Co.

If present, MMP inhibitors generally comprise at least about 0.001% by weight of the compositions of the present invention.

Anti-Oxidants, Vitamins and Nutrients

Modifiers of cell redox status include anti-oxidants such as N-acetyl cysteine and gallic acid; anti-oxidant enzyme inducers such as anethole-dithiothione, oltipraz, pyrrolidine dithiocarbamate (PDTC) and indole-3-carbinol; nutrients and vitamins such as Co-enzyme Q10, pyrroloquinoline quinone (PQQ), vitamins A, C, and E, selenium and combinations thereof.

Orally Acceptable Carrier Materials

The orally acceptable carrier comprises one or more compatible solid or liquid excipients or diluents which are suitable for topical oral administration. By "compatible," as used herein, is meant that the components of the composition are capable of being commingled without interaction in a manner which would substantially reduce the composition's stability and/or efficacy. Such materials are well known in the art and are readily chosen by one skilled in the art based on the physical, aesthetic and performance properties desired for the compositions being prepared. These carriers may be included at levels typically from about 50% to about 99%, preferably from about 70% to about 98%, and more preferably from about 90% to about 95%, by weight of the oral composition.

The carriers or excipients of the present invention can include the usual and conventional components of dentifrices, non-abrasive gels, subgingival gels, mouthwashes or rinses, mouth sprays, chewing gums, lozenges and breath mints as more fully described hereinafter.

The choice of a carrier to be used is basically determined by the way the composition is to be introduced into the oral cavity. Carrier materials for toothpaste, tooth gel or the like include abrasive materials, sudsing agents, binders, humectants, flavoring and sweetening agents, etc. as disclosed in e.g., U.S. Pat. No. 3,988,433, to Benedict. Carrier materials for biphasic dentifrice formulations are disclosed in U.S. Pat. Nos. 5,213,790, issued May 23, 1993, 5,145,666, issued Sep. 8, 1992, and 5,281,410 issued Jan. 25, 1994 all to Lukacovic et al. and in U.S. Pat. Nos. 4,849,213 and 4,528,180 to Schaeffer. Mouthwash, rinse or mouth spray carrier materials typically include water, flavoring and sweetening agents, etc., as disclosed in, e.g., U.S. Pat. No. 3,988,433 to Benedict. Lozenge carrier materials typically include a candy base; chewing gum carrier materials include a gum base, flavoring and sweetening agents, as in, e.g., U.S. Pat. No. 4,083,955, to Grabenstetter et al. Sachet carrier materials typically include a sachet bag, flavoring and sweetening agents. For subgingival gels used for delivery of actives into the periodontal pockets or around the periodontal pockets, a "subgingival gel carrier" is chosen as disclosed in, e.g. U.S. Pat. Nos. 5,198,220 and 5,242,910, issued Mar. 30, 1993 and Sep. 7, 1993, respectively both to Damani. Carriers suitable for the preparation of compositions of the present invention are well known in the art. Their selection will depend on secondary considerations like taste, cost, and shelf stability, etc.

The compositions of the present invention may also be in the form of non-abrasive gels and subgingival gels, which may be aqueous or non-aqueous. In still another aspect, the invention provides a dental implement impregnated with the present composition. The dental implement comprises an implement for contact with teeth and other tissues in the oral cavity, the implement being impregnated with the present composition. The dental implement can be impregnated fibers including dental floss or tape, chips, strips, films and polymer fibers.

In a preferred embodiment, the compositions of the subject invention are in the form of dentifrices, such as toothpastes, tooth gels and tooth powders. Components of such toothpaste and tooth gels generally include one or more of a dental abrasive (from about 6% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpaste or tooth gel may also include one or more of an anticaries agent (from about 0.05% to about 0.3% as fluoride ion) and an anticalculus agent (from about 0.1% to about 13%). Tooth powders, of course, contain substantially all non-liquid components.

Other preferred embodiments of the subject invention are liquid products, including mouthwashes or rinses, mouth sprays, dental solutions and irrigation fluids. Components of such mouthwashes and mouth sprays typically include one or more of water (from about 45% to about 95%), ethanol (from about 0% to about 25%), a humectant (from about 0% to about 50%), a surfactant (from about 0.01% to about 7%), a flavoring agent (from about 0.04% to about 2%), a sweetening agent (from about 0.1% to about 3%), and a coloring agent (from about 0.001% to about 0.5%). Such mouthwashes and mouth sprays may also include one or more of an anticaries agent (from about 0.05% to about 0.3% as fluoride ion) and an anticalculus agent (from about 0.1% to about 3%). Components of dental solutions generally include one or more of water (from about 90% to about 99%), preservative (from about 0.01% to about 0.5%), thickening agent (from 0% to about 5%), flavoring agent (from about 0.04% to about 2%), sweetening agent (from about 0.1% to about 3%), and surfactant (from 0% to about 5%).

Examples of suitable carrier materials for the present compositions are described in the following paragraphs.

Fluoride Ion Sources

The oral compositions of the present invention will optionally include a soluble fluoride source capable of providing bioavailable and efficacious fluoride ions. Soluble fluoride ion sources include sodium fluoride, stannous fluoride, indium fluoride, amine fluoride and sodium monofluorophosphate. Stannous fluoride is a preferred soluble fluoride source. This ingredient may serve as both a/the stannous ion source and fluoride source. Norris et al., U.S. Pat. No. 2,946,725, issued Jul. 26, 1960, and Widder et al., U.S. Pat. No. 3,678,154 issued Jul. 18, 1972, disclose such fluoride sources as well as others.

The present compositions may contain a soluble fluoride ion source capable of providing from about 50 ppm to about 3500 ppm, and preferably from about 500 ppm to about 3000 ppm of free fluoride ions. To deliver the desired amount of fluoride ions, fluoride ion sources may be present in the total oral composition at an amount of from about 0.1% to about 5%, preferably from about 0.2% to about 1%, and more preferably from about 0.3% to about 0.6%, by weight of the total composition delivered to the oral cavity.

Peroxide Source

The present invention may include a peroxide source in the composition. In addition to whitening, peroxide also provides other benefits to the oral cavity. It has long been recognized that hydrogen peroxide and other peroxygen-compounds are effective in curative and/or prophylactic treatments with respect to caries, dental plaque, gingivitis, periodontitis, mouth odor, recurrent aphthous ulcers, denture irritations, orthodontic appliance lesions, postextraction and postperiodontal surgery, traumatic oral lesions and mucosal infections, herpetic stomatitis and the like. Peroxide-containing agents in the oral cavity exert a chemomechanical action generating thousands of tiny oxygen bubbles produced by interaction with tissue and salivary enzymes. The swishing action of a mouthrinse enhances this inherent chemomechanical action. Such action has been recommended for delivery of other agents into infected gingival crevices. Peroxide thus prevents colonization and multiplication of anaerobic bacteria known to be associated with periodontal disease and is among the preferred antibacterials for use herein.

The peroxide source is selected from the group consisting of hydrogen peroxide, calcium peroxide, urea peroxide, and mixtures thereof. The following amounts represent the amount of peroxide raw material, although the peroxide source may contain ingredients other than the peroxide raw material. The present composition may contain from about 0.01% to about 10%, preferably from about 0.1% to about 5%, more preferably from about 0.2% to about 3%, and most preferably from about 0.3% to about 0.8% of a peroxide source, by weight of the oral composition.

Alkali Metal Bicarbonate Salt

The present invention may also include an alkali metal bicarbonate salt. Sodium bicarbonate, also known as baking soda, is the preferred alkali metal bicarbonate salt. As indicated above, baking soda has some antibacterial and anti-inflammatory activity and thus may be used as an active ingredient. The alkali metal bicarbonate salt also functions as a buffering agent. The present composition may contain from about 0.5% to about 50%, preferably from about 0.5% to about 30%, more preferably from about 2% to about 20%, and most preferably from about 5% to about 18% of an alkali metal bicarbonate salt, by weight of the oral composition.

Anticalculus Agent

The present compositions may optionally include an anticalculus agent, which are materials with chelating activity and effective in reducing mineral deposition related to calculus formation. Such chelating agents are able to complex calcium found in the cell walls of the bacteria and can also disrupt plaque by removing calcium from the calcium bridges which help hold this biomass intact. However, it is not desired to use a chelating agent which has an affinity for calcium that is too high, as this may result in tooth demineralization, which is contrary to the objects and intentions of the present invention. Suitable chelating agents will generally have a calcium binding constant of about $10^1$ to $10^5$ to provide improved cleaning with reduced plaque and calculus formation. Chelating agents also have the ability to complex with metallic ions and thus can be used to stabilize stannous if present in the compositions.

Such chelating agents useful for their anticalculus activity include pyrophosphates, tripolyphosphates, and diphosphonates such as EHDP and AHP. The pyrophosphate salts useful as a source of pyrophosphate ion in the present compositions include the dialkali metal pyrophosphate salts, tetraalkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, from about 1.5% to about 10% in one embodiment, and from about 2% to about 6% in another embodiment. Free pyrophosphate ions may be present in a variety of protonated states depending on the pH of the composition.

Compositions comprising predominately undissolved pyrophosphate refer to compositions containing no more than about 20% of the total pyrophosphate salt dissolved in the composition, preferably less than about 10% of the total pyrophosphate dissolved in the composition. Tetrasodium pyrophosphate salt is the preferred pyrophosphate salt in these compositions. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, generally from about 1.5% to about 15%, preferably from about 2% to about 10%, and most preferably from about 3% to about 8%, by weight of the dentifrice composition.

Compositions may also comprise a mixture of dissolved and undissolved pyrophosphate salts. Any of the above mentioned pyrophosphate salts may be used.

The pyrophosphate salts are described in more detail in Kirk-Othmer *Encyclopedia of Chemical Technology*, Third Edition, Volume 17, Wiley-Interscience Publishers (1982).

Other examples of chelating agents used as anticalculus agent include ethylenediaminetetraacetic acid, nitrilotriacetic acid and related compounds disclosed in British Patent 490,384, Feb. 15, 1937; polyphosphonates in U.S. Pat. No. 3,678,154, Jul. 18, 1972 to Widder et al., U.S. Pat. No. 5,338,537 issued to Aug. 16, 1994 to White, Jr., and U.S. Pat. No. 5,451,401 issued Sep. 19, 1995 to Zerby et al.; carbonyl diphosphonates in U.S. Pat. No. 3,737,533, Jun. 5, 1973 to Francis; a zinc-polymer combination formed by the reaction or interaction of a zinc compound with an anionic polymer containing carboxylic, sulfonic and/or phosphonic acid radicals in U.S. Pat. No. 4,138,477, issued Feb. 6, 1979, to Gaffar; tartaric acid in U.S. Pat. Nos. 5,849,271 issued Dec. 15, 1998 and 5,622,689 issued Apr. 22, 1997 both to Lukacovic; acid or salt form of tartrate monosuccinate, tartrate disuccinate, and mixtures thereof in U.S. Pat. No. 5,015,467 issued May 14, 1991 to Smitherman; acrylic acid polymer or copolymer in U.S. Pat. No. 4,847,070, Jul. 11, 1989 to Pyrz et al. and in U.S. Pat. No. 4,661,341, Apr. 28, 1987 to Benedict et al.; sodium alginate in U.S. Pat. No. 4,775,525, issued Oct. 4, 1988, to Pera; polyvinyl pyrrolidone in GB 741,315 published Nov. 30, 1955, WO 99/12517 published Mar. 18, 1999 and U.S. Pat. No. 5,538,714 issued Jul. 23, 1996 to Pink et al.; and copolymers of vinyl pyrrolidone with carboxylates in U.S. Pat. No. 5,670,138 issued Sep. 23, 1997 to Venema et al. and in JP Publication No. 2000-0633250 to Lion Corporation, published Feb. 29, 2000. Other chelating agents that may be used as anticalculus agents include gluconic acid, tartaric acid, citric acid and pharmaceutically-acceptable salts thereof. Examples include sodium or potassium gluconate and citrate; citric acid/alkali metal citrate combination; zinc citrate trihydrate; disodium tartrate; dipotassium tartrate; sodium potassium tartrate; sodium hydrogen tartrate; potassium hydrogen tartrate. The amounts of such chelating agents suitable for use in the present invention are about 0.1% to about 2.5%, preferably from about 0.5% to about 2.5% and more preferably from about 1.0% to about 2.5%.

Still other anticalculus agents suitable for use in the present invention are the polymeric polycarboxylates disclosed in U.S. Pat. No. 4,138,477, Feb. 6, 1979 and U.S. Pat. No. 4,183,914, Jan. 15, 1980 to Gaffar et al. and include copolymers of maleic anhydride or acid with another polymerizable ethylenically unsaturated monomer, such as methyl vinyl ether (methoxyethylene), styrene, isobutylene or ethyl vinyl ether. Such materials are well known in the art, being employed in the form of their free acids or partially or preferably fully neutralized water soluble alkali metal (e.g. potassium and preferably sodium) or ammonium salts. Examples are 1:4 to 4:1 copolymers of maleic anhydride with methyl vinyl ether having a molecular weight (M.W.) of about 30,000 to about 1,000,000. These copolymers are available for example as Gantrez AN 139 (M.W. 500,000), AN 119 (M.W. 250,000) and S-97 Pharmaceutical Grade (M.W. 70,000), of GAF Chemicals Corporation.

Other operative polymeric polycarboxylates include the 1:1 copolymers of maleic anhydride with ethyl acrylate, hydroxyethyl methacrylate, N-vinyl-2-pyrrolidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Abrasives

Dental abrasives useful in the topical, oral carriers of the compositions of the subject invention include many different materials. The material selected must be one which is compatible within the composition of interest and does not excessively abrade dentin. Suitable abrasives include, for example, silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, and resinous abrasive materials such as particulate condensation products of urea and formaldehyde.

Another class of abrasives for use in the present compositions is the particulate thermo-setting polymerized resins as described in U.S. Pat. No. 3,070,510 issued to Cooley & Grabenstetter on Dec. 25, 1962. Suitable resins include, for example, melamines, phenolics, ureas, melamine-ureas, melamine-formaldehydes, urea-formaldehyde, melamine-urea-formaldehydes, cross-linked epoxides, and cross-linked polyesters.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975. Examples include the silica xerogels marketed under the trade name "Syloid" by the W.R. Grace & Company, Davison Chemical Division and precipitated silica materials such as those marketed by the J. M. Huber Corporation under the trade name, Zeodent®, particularly the silicas carrying the designation Zeodent® 119, Zeodent® 118, Zeodent® 109 and Zeodent® 129. The types of silica dental abrasives useful in the toothpastes of the present invention are described in more detail in Wason, U.S. Pat. No. 4,340,583, issued Jul. 29, 1982; and in commonly-assigned U.S. Pat. No. 5,603,920, issued on Feb. 18, 1997; U.S. Pat. No. 5,589,160, issued Dec. 31, 1996; U.S. Pat. No. 5,658,553, issued Aug. 19, 1997; U.S. Pat. No. 5,651,958, issued Jul. 29, 1997, and U.S. Pat. No. 6,740,311, issued May 25, 2004.

Mixtures of abrasives can be used such as mixtures of the various grades of Zeodent® silica abrasives listed above. The total amount of abrasive in dentifrice compositions of the subject invention typically range from about 6% to about 70% by weight; toothpastes preferably contain from about 10% to about 50% of abrasives, by weight of the composition. Dental solution, mouth spray, mouthwash and non-abrasive gel compositions of the subject invention typically contain little or no abrasive.

Water Content

Water employed in the preparation of commercially suitable oral compositions should preferably be of low ion content and free of organic impurities. In the oral composition, water may comprise from 0% up to about 95%, and preferably from about 5% to about 50%, by weight of the composition herein. The amounts of water include the free water which is added plus that which is introduced with other materials, such as with sorbitol, silica, surfactant solutions, and/or color solutions.

Buffering Agent

The present compositions may contain a buffering agent. Buffering agents, as used herein, refer to agents that can be used to adjust the pH of the compositions to a range of about pH 3.0 to about pH 10.

Suitable buffering agents include alkali metal hydroxides, carbonates, sesquicarbonates, borates, silicates, phosphates, imidazole, and mixtures thereof. Specific buffering agents include monosodium phosphate, trisodium phosphate, sodium benzoate, benzoic acid, sodium hydroxide, potassium hydroxide, alkali metal carbonate salts, sodium carbonate, imidazole, pyrophosphate salts, citric acid, and sodium citrate. Preferred buffers would be those that control the pH in the target range without complexing active agents such as stannous ions. Preferred buffering agents include acetic acid, sodium acetate, citric acid, sodium citrate, benzoic acid and sodium benzoate. Buffering agents are used at a level of from about 0.1% to about 30%, preferably from about 1% to about 10%, and more preferably from about 1.5% to about 3%, by weight of the present composition.

Thickening Agents

In preparing toothpaste or gels, it is necessary to add some thickening material to provide a desirable consistency of the composition, to provide desirable active agent release characteristics upon use, to provide shelf stability, and to provide stability of the composition, etc. Preferred thickening agents are carboxyvinyl polymers, carrageenan, hydroxyethyl cellulose, laponite and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture.

A preferred class of thickening or gelling agents includes a class of homopolymers of acrylic acid crosslinked with an alkyl ether of pentaerythritol or an alkyl ether of sucrose, or carbomers. Carbomers are commercially available from B.F. Goodrich as the Carbopol® series. Particularly preferred carbopols include Carbopol 934, 940, 941, 956, and mixtures thereof.

Copolymers of lactide and glycolide monomers, the copolymer having the molecular weight in the range of from about 1,000 to about 120,000 (number average), are useful for delivery of actives into the periodontal pockets or around the periodontal pockets as a "subgingival gel carrier." These polymers are described in U.S. Pat. No. 5,198,220, issued Mar. 30, 1993 and U.S. Pat. No. 5,242,910, issued Sep. 7, 1993 both to Damani, and U.S. Pat. No. 4,443,430, issued Apr. 17, 1984 to Mattei.

Thickening agents in an amount from about 0.1% to about 15%, preferably from about 2% to about 10%, more preferably from about 4% to about 8%, by weight of the total toothpaste or gel composition, can be used. Higher concentrations can be used for chewing gums, lozenges, breath mints, sachets, non-abrasive gels and subgingival gels.

Humectants

Another optional component of the topical, oral carriers of the compositions of the subject invention is a humectant. The humectant serves to keep toothpaste compositions from hardening upon exposure to air, to give compositions a moist feel to the mouth, and, for particular humectants, to impart desirable sweetness of flavor to toothpaste compositions. The humectant, on a pure humectant basis, generally comprises from about 0% to about 70%, preferably from about 5% to about 25%, by weight of the compositions herein. Suitable humectants for use in compositions of the subject invention include edible polyhydric alcohols such as glycerin, sorbitol, xylitol, butylene glycol, polyethylene glycol, and propylene glycol, especially sorbitol and glycerin.

Flavoring and Sweetening Agents

Flavoring agents can also be added to the compositions. Suitable flavoring agents include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof. Flavoring agents are generally used in the compositions at levels of from about 0.001% to about 5%, by weight of the composition.

Sweetening agents which can be used include sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof. A composition preferably contains from about 0.1% to about 10% of these agents, preferably from about 0.1% to about 1%, by weight of the composition.

In addition to flavoring and sweetening agents, coolants, salivating agents, warming agents, and numbing agents can be used as optional ingredients in compositions of the present invention. These agents are present in the compositions at a level of from about 0.001% to about 10%, preferably from about 0.1% to about 1%, by weight of the composition.

The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred coolants are selected from the group consisting of menthol, 3-1-menthoxypropane-1,2-diol known as TK-10 manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979.

Preferred salivating agents of the present invention include Jambu® manufactured by Takasago. Preferred warming agents include capsicum and nicotinate esters, such as benzyl nicotinate. Preferred numbing agents include benzocaine, lidocaine, clove bud oil, and ethanol.

Surfactants

The present compositions may also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976.

Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene, polyoxyethylene sorbitan esters (sold under trade name Tweens), Polyoxyl 40 hydrogenated castor oil, fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The nonionic surfactant poloxamer 407 is one of the most preferred surfactant because the poloxamer may also function as an emulsifying agent, binder, stabilizer and to reduce the astringency of metal ions such as stannous and zinc. Poloxamers are difunctional block-polymers terminating in primary hydroxyl groups with molecular weights ranging from 1,000 to above 15,000. Poloxamers are sold under the tradename of Pluronics and Pluraflo by BASF. Suitable poloxamers for this invention are Poloxamer 407 and Pluraflo L4370.

The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of the suitable nonionic and amphoteric surfactants are disclosed by Gieske et al., U.S. Pat. No. 4,051,234, issued Sep. 27, 1977. The present composition typically comprises one or more surfactants each at a level of from about 0.25% to about 12%, preferably from about 0.5% to about 8%, and most preferably from about 1% to about 6%, by weight of the composition.

Additional Carrier Materials

Other emulsifying agents that may be used in the present compositions include polymeric emulsifiers such as the Pemulen® series available from B.F. Goodrich, and which are predominantly high molecular weight polyacrylic acid polymers useful as emulsifiers for hydrophobic substances.

Titanium dioxide may also be added to the present composition. Titanium dioxide is a white powder which adds opacity to the compositions. Titanium dioxide generally comprises from about 0.25% to about 5% by weight of dentifrice compositions.

Coloring agents may also be added to the present composition. The coloring agent may be in the form of an aqueous solution, preferably 1% coloring agent in a solution of water. Color solutions generally comprise from about 0.01% to about 5%, by weight of the composition.

Other optional agents that may be used in the present compositions include dimethicone copolyols selected from alkyl- and alkoxy-dimethicone copolyols, such as C12 to C20 alkyl dimethicone copolyols and mixtures thereof. Highly preferred is cetyl dimethicone copolyol marketed under the trade name Abil EM90. The dimethicone copolyol is generally present in a level of from about 0.01% to about 25%, preferably from about 0.1% to about 5%, more preferably from about 0.5% to about 1.5% by weight. The dimethicone copolyols aid in providing positive tooth feel benefits.

Composition Use

A safe and effective amount of the compositions of the present invention comprising the combination of one or more antibacterial agents and anti-inflammatory agents may be topically applied to the mucosal tissue of the oral cavity, to the gingival tissue of the oral cavity, and/or to the surface of the teeth, for the treatment or prevention of the above mentioned diseases or conditions of the oral cavity of subjects, in several conventional ways. The subject may be any person or animal in need of treatment or prevention of oral conditions including plaque, gingivitis, and periodontitis. By "animal" is meant to include in particular household pets or other domestic animals, or animals kept in captivity.

For example, the gingival or mucosal tissue may be rinsed with a solution (e.g., mouth rinse, mouth spray); or if the composition is a dentifrice (e.g., toothpaste, tooth gel or tooth powder), the gingival/mucosal tissue or teeth is bathed in the liquid and/or lather generated by brushing the teeth. Other non-limiting examples include applying a non-abrasive gel or paste directly to the gingival/mucosal tissue or to the teeth with or without an oral care appliance described below; chewing gum; chewing or sucking on a breath tablet or lozenge. Preferred methods of topical oral application of the present compositions are via rinsing with a mouth rinse solution and via brushing with a dentifrice. Other methods of topically applying the present compositions to the gingival/mucosal tissue and the surfaces of the teeth are apparent to those skilled in the art.

The concentrations of antibacterial agent and anti-inflammatory agent in the compositions of the present invention depend on the type of composition (e.g., toothpaste, mouth rinse, lozenge, gum, etc.) used to apply composition to the gingival/mucosal tissue and/or the teeth, due to differences in efficiency of the compositions contacting the tissue and teeth, and due also to the amount of the composition generally used. The concentration will also depend on the specific agents being used and on the disease or condition being treated. Typically the antibacterial agent will be present in the compositions from about 0.01% to about 20% by weight and the anti-inflammatory agent from about 0.001% to about 10% by weight. These amounts refer to the amount of antibacterial or anti-inflammatory active agents in the source used. For example, tea polyphenols may be incorporated in the composition as a tea extract which will typically contain other components such as tannic acid, caffeine, vitamins and polysaccharides. The tea polyphenols may comprise from 85% to 95% of the extract.

The present compositions are preferably applied to the gingival/mucosal tissue and/or the teeth (for example, by rinsing with a mouthrinse, directly applying a non-abrasive gel with or without a device, applying a dentifrice or a tooth gel with a toothbrush, sucking or chewing a lozenge or breathmint, etc.) preferably for at least about 10 seconds, preferably from about 20 seconds to about 10 minutes, more preferably from about 30 seconds to about 60 seconds. The method often involves expectoration of most of the composition following such contact. The frequency of such contact is preferably from about once per week to about four times per day, more preferably from about thrice per week to about three times per day, even more preferably from about once per day to about twice per day. The period of such treatment typically ranges from about one day to a lifetime. For particular oral care diseases or conditions the duration of treatment depends on the severity of the oral disease or condition being treated, the particular delivery form utilized and the patient's response to treatment. If delivery to the periodontal pockets is desirable, such as with the treatment of periodontal disease, a mouthrinse can be delivered to the periodontal pocket using a syringe or water injection device. These devices are known to one skilled in the art. Devices of this type include "Water Pik" by Teledyne Corporation. After irrigating, the subject can swish the rinse in the mouth to also cover the dorsal tongue and other gingival and mucosal surfaces. In addition a toothpaste, non-abrasive gel, toothgel, etc. can be brushed onto the tongue surface and other gingival and mucosal tissues of the oral cavity.

The present compositions may also be delivered to tissues and/or spaces within the oral cavity using electromechanical devices such as metering devices, targeted application devices and cleaning or integrated oral hygiene systems.

For treating oral tissue wounds and aiding tissue regeneration, fluid subgingival gel compositions that can be inserted via syringe and either a needle or catheter directly into the areas needing treatment, such as the periodontal cavities, are very useful and convenient. Preferred gel-like fluid compositions are those that transform into near solid phase in the presence of aqueous fluid such as water or crevicular fluid, such gels typically comprising from 0.02% to 6% of the active agent(s) in a carrier system comprising a poly(lactyl-co-glycolide) copolymer and solvent such as propylene carbonate. The hardened composition is thus retained at the site of application, and since the polymeric carrier undergoes slow degradation via hydrolysis, the active agent(s) continue to release in a sustained manner from such compositions.

Pet care products such as foods, chews and toys may be formulated to contain the the present compositions. The active agent(s) may be incorporated for example, into a relatively supple but strong and durable material such as rawhide, ropes made from natural or synthetic fibers, and polymeric articles made from nylon, polyester or thermoplastic polyurethane. As the animal chews, licks or gnaws the product, incorporated active agents are released into the animal's oral cavity into a salivary medium, comparable to an effective brushing or rinsing. In pet food embodiments, the active agent(s) may be incorporated as an ingredient or admixed into a pet food such as for example, a kibbled, semi-moist, or canned food. Highly preferred food embodiments include carriers that tend to increase residence time of the food in the oral cavity. For example, the active agent can be incorporated in a carrier that will tend to stick or adhere to the teeth, in order that a certain amount of product will remain in the mouth and not be ingested immediately. The present compositions may also be incorporated into other pet care products including nutritional supplements and drinking water additives.

The following non-limiting examples further describe preferred embodiments within the scope of the present invention. The examples are given solely for illustration and are not to be construed as limitations of this invention as many variations thereof are possible without departing from the spirit and scope thereof.

EXAMPLES

Example I

Mouthrinse Compositions

The following oral care mouthrinse compositions according to the present invention are shown below with amounts of components in weight % These compositions are made using conventional methods.

| Component | IA | IB | IC | ID | IE | IF | IG | IH |
|---|---|---|---|---|---|---|---|---|
| Riboflavin 5'-monophosphate | 0.026 | 0.026 | 0.026 | 0.078 | 0.026 | — | — | 0.026 |
| EGCG | — | — | — | — | — | 0.100 | 0.100 | 0.100 |
| Cetylpyridinium Chloride (CPC) | 0.035 | 0.070 | 0.070 | 0.050 | 0.045 | 0.075 | 0.065 | 0.075 |
| Domiphen Bromide (DB) | — | — | — | — | 0.005 | — | — | — |
| Zinc Lactate | — | — | — | 0.250 | — | — | — | 0.050 |
| $H_2O_2$ 35% soln. | — | 2.145 | — | — | — | — | — | — |
| Flavor/Coolant | 0.080 | 0.210 | 0.120 | 0.160 | 0.080 | 0.120 | 0.200 | 0.070 |
| Glycerin | 23.000 | 20.000 | 23.000 | 13.000 | 5.000 | 5.000 | 13.000 | 18.000 |
| Saccharin | 0.025 | 0.060 | 0.018 | 0.030 | 0.025 | 0.030 | 0.010 | 0.013 |
| Sucralose | | | | | | | | 0.008 |
| Poloxamer 407 | — | 0.100 | 0.050 | 0.025 | — | 0.050 | 0.050 | 0.001 |
| Propylene Glycol | | 4.000 | | | | | | |
| Monosodium Phosphate | 0.085 | 0.050 | — | — | — | 0.085 | 0.050 | 0.053 |
| Dibasic Sodium Phosphate | 0.070 | 0.020 | — | — | — | 0.070 | 0.020 | 0.020 |
| Color | 0.020 | 0.020 | 0.010 | 0.020 | 0.020 | 0.020 | 0.020 | 0.020 |
| Ethanol | — | — | — | 1.200 | 5.000 | — | — | — |
| Methylparaben | | | | | | | | 0.020 |
| Propylparaben | | | | | | | | 0.005 |
| Water | QS | QS | QS | QS | QS | QS | QS | QS |

Example II

Dentifrice Compositions

Dentifrice compositions according to the present invention are shown below with amounts of components in weight %. These compositions are made using conventional methods.

| Component | IIA | IIB | IIC | IID | IIE | IIF |
|---|---|---|---|---|---|---|
| Stannous Fluoride | 0.454 | 0.454 | | 0.454 | 0.454 | 0.454 |
| Stannous Chloride | | | 1.500 | | | 1.500 |
| Zinc Carbonate | 2.000 | | | | | |
| Zinc Oxide | | | 5.000 | | | |
| Zinc Citrate | | | | 0.400 | | |
| Zinc Lactate | | | | | 2.500 | |
| Triclosan | | 0.280 | | | | |
| Riboflavin 5'-monophosphate | | 0.100 | 1.000 | 0.400 | | |
| EGCG | | | | | | 1.000 |
| Tea Extract | 2.000 | 2.000 | | | | |
| Eugenol | | | | | 0.100 | |
| Vitamin C | 1 | 0.050 | | | | |
| Vitamin E | | 0.010 | | | | |
| Phytic Acid (20% Soln) | 4.000 | | | | | |
| Sodium Phytate (20% Soln.) | | | 10.000 | | | |
| Na Polyphosphate | | | | | 13.000 | |
| Tetra Na Pyrophosphate | | 0.740 | | | | |
| Tetra K Pyrophosphate | | 1.985 | | | | |
| Sodium Acid Pyrophoshate | | 3.500 | | | | |
| Gantrez S97 | | | | 1.000 | | |
| Sodium Fluoride | | | 0.243 | | | |
| Carbomer 956 | | 0.250 | | | | |
| Sodium Gluconate | 0.670 | | | 0.670 | 0.650 | 2.100 |
| Sorbitol Soln | 34.275 | 27.910 | 34.275 | 16.275 | | 37.496 |
| Glycerin | | 7.000 | | 5.000 | 35.800 | 14.425 |
| Hydroxyethyl cellulose | 0.300 | | 0.300 | | | |
| Na CMC | 1.200 | | 1.200 | | | 0.600 |
| Carrageenan | 0.500 | | 0.500 | | 0.600 | |
| Xanthan Gum | | 0.900 | | | 0.350 | 0.700 |
| Polyethylene Glycol | | 6.000 | | 0.400 | 7.000 | |
| Propylene Glycol | | | | | 7.000 | |
| Silica Abrasive | 20.000 | 20.000 | 20.000 | | 25.000 | 20.000 |
| Ca Pyrophosphate | | | | 40.00 | | |
| TiO$_2$ (Anatase) | 0.525 | 3.940 | 0.525 | | | 0.525 |
| SLS (28% Soln.) | 4.000 | 7.500 | 4.000 | 2.800 | 2.500 | 5.000 |
| Na Saccharin | 0.250 | 0.370 | 0.250 | 0.200 | 0.500 | 0.300 |
| Flavor | 0.950 | 1.000 | 0.950 | 1.000 | 0.800 | 1.000 |
| NaOH | 0.006 | | 0.006 | 0.450 | | 0.600 |
| Na Phosphate Tribasic | | | | | 1.100 | |
| Water and Minors, e.g., Color soln., Preservative | QS | QS | QS | QS | QS | QS |

Example III

In Vivo Efficacy Testing

A study was conducted to evaluate the in vivo efficacy of a riboflavin+cetyl pyridinium chloride (CPC) rinse in a canine model. At the beginning of the study beagle subjects received a prophylaxis. Approximately one week later, they were graded for baseline Gingival Index (GI) and Plaque Index. Gingival Index is a 0-3 scale (0=no inflammation; 1=inflammation present, gingiva is red; 2=bleeding upon probing; 3=spontaneous bleeding). Plaque Index is percent plaque coverage of each tooth. The dogs were randomly allocated into treatment groups balanced on baseline inflammation index (II) scores using a SAS randomization program. Treatments began the day after allocation. The animals were treated topically on the teeth/gingiva with a spray mist bottle twice daily during the week and once daily on weekends for thirty days (30 ml/treatment). At the end of thirty days, the animals received final clinical grading.

Clinical gradings were done at baseline and final evaluation. For gingival index, the buccal surfaces of the following teeth in all four quadrants were measured for a total of twenty teeth: first molar, fourth, third and second premolars and first canine. Three scores were determined for each tooth for sixty scores. The maximum score of the three buccal surfaces per tooth was recorded. Then the average of these scores was computed (Mean Tooth-Level Score). The data were analyzed with analysis of covariance (ANCOVA), with the respective baseline as the model covariate using the Statistical Analysis System (SAS). Plaque was measured by percent coverage of each tooth. The plaque is disclosed with a 1% basic fuchsin solution applied with a cotton tipped applicator. Water is sprayed to remove excessive staining solution. The percentage of purple is also recorded in 5% increments for each tooth. The plaque data were analyzed using analysis of variance (ANOVA). Results are summarized below.

These results demonstrate that the combination of an anti-inflammatory agent (riboflavin) and an anti-bacterial agent (CPC) provides enhanced anti-plaque and anti-gingivitis efficacy. Indeed the combination provides efficacy even at lower levels of CPC. This is advantageous since quaternary ammonium antimicrobials such as CPC while efficacious, are known to impart unpleasant taste and to cause staining or discoloration of teeth particularly at concentrations that have been employed to provide efficacy. By using such lower levels, the unpleasant taste and the tendency to cause dental stain will both be avoided. The present compositions therefore may not need the anti-staining and taste-masking additives that have been used in the art to address the negative aspects associated with CPC.

| Treatment | Analysis of Covariance Gingival Index (Modified Löe-Silness) Mean of Maximum Score Per Tooth | | | Analysis of Variance Plaque Index | |
|---|---|---|---|---|---|
| | N | Adj. Mean Tooth-Level Score | Adj. Sum of Scores | N | Mean Plaque Score |
| Water | 9 | 1.40 | 28.0 | 9 | 81.65 |
| Riboflavin 0.078% | 9 | 1.31 | 26.3 | 9 | 80.61 |
| 0.07% CPC | 9 | 1.18 | 23.7 | 9 | 55.53 |
| 0.035% CPC + 0.078% Riboflavin | 9 | 1.16 | 23.3 | 9 | 64.89 |
| 0.07%/CPC + 0.078% Riboflavin | 9 | 1.16 | 23.1 | 9 | 57.68 |
| 0.035% CPC + 0.026% Riboflavin | 9 | 1.13 | 22.5 | 9 | 68.47 |

Baseline Tooth-Level GI Mean = 0.83

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A topical oral composition comprising in an orally-acceptable carrier a combination of
   (a) from about 0.001% to about 10% by weight of the composition of two or more of anti-inflammatory agents having inhibitory activity against two or more of host pro-inflammatory factors selected from matrix metalloproteinases (MMP's), cyclooxygenases (COX), $PGE_2$, interleukin 1 (IL-1), or nuclear factor kappa B (NF-κB) and
   (b) from about 0.01% to about 20% by weight of the composition of one or more of an antibacterial agent having inhibitory activity against one or more bacterial species selected from *Porphyromonas gingivalis, Bacteroides forsythus* or *Actinobacillus actinomycetemcomitans* and bacterial virulence factors selected from biofilm formation or biofilm adherence,
   wherein the combination is present in an amount effective to provide enhanced efficacy to treat and prevent bacteria-mediated oral cavity conditions, with the proviso that the composition does not comprise other anti-inflammatory agents selected from aspirin, ibuprofen, flurbiprofen or indomethacin.

2. A topical oral composition according to claim 1, wherein the two or more anti-inflammatory agents are selected from riboflavin, riboflavin phosphate, curcumin, eugenol, dihydroeugenol, thymol, carvacrol, citral, cymen-5-ol, geraniol, eucalyptol, cinnamaldehyde, anthocyanidine, baicalein, tannic acid, quercetin, folic acid, hexamidine, epigallocatechin, epigallocatechin gallate (EGCG) or berberine.

3. A topical oral composition according to claim 1, wherein the antibacterial agent is one or a mixture of cetyl pyridinium chloride (CPC), stannous ion source, zinc ion source, copper ion source, iron ion source, ascorbyl stearate, oleoyl sarcosine, alkyl sulfate or dioctyl sulfosuccinate.

4. A topical oral composition according to claim 1 wherein said composition is in a form selected from mouthrinse, toothpaste, tooth gel, tooth powder, non-abrasive gel, mousse, foam, chewing gum, mouth spray, lozenge, oral tablet, dental implement or pet care product.

5. A topical oral composition according to claim 1 further comprising a host-response modulating agent which is a cell redox status modifier selected from one or a mixture of Co-enzyme Q10, pyrroloquinoline quinone (PQQ), Vitamin C, Vitamin E, Vitamin A or anethole-dithiothione.

6. A topical oral composition according to claim 1 wherein said composition comprises an additional therapeutic active selected from one or a mixture of antimicrobial/antiplaque agents, biofilm inhibiting agents, antibiotics; analgesics, local anesthetic agents, dentinal desensitizing agents or odor masking agents.

* * * * *